(12) United States Patent
Nettekoven et al.

(10) Patent No.: US 7,786,109 B2
(45) Date of Patent: Aug. 31, 2010

(54) TRICYCLIC AMIDE DERIVATIVES AS MODULATORS OF H3 RECEPTORS

(75) Inventors: Matthias Nettekoven, Grenzach-Wyhlen (DE); Jean-Marc Plancher, Hagenthal-le-Bas (FR); Hans Richter, Grenzach-Wyhlen (DE); Olivier Roche, Folgensbourg (FR); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/389,619

(22) Filed: Feb. 20, 2009

(65) Prior Publication Data

US 2009/0156583 A1 Jun. 18, 2009

Related U.S. Application Data

(62) Division of application No. 11/605,899, filed on Nov. 29, 2006, now Pat. No. 7,579,351.

(30) Foreign Application Priority Data

Dec. 9, 2005 (EP) .................................. 05111879

(51) Int. Cl.
C07D 487/14 (2006.01)
(52) U.S. Cl. ...................... 514/220; 540/561
(58) Field of Classification Search .............. 540/561
See application file for complete search history.

(56) References Cited

U.S. PATENT DOCUMENTS

| | | | |
|---|---|---|---|
| 4,598,089 | A | 7/1986 | Hadvary et al. |
| 4,931,463 | A | 6/1990 | Barbier et al. |
| 4,983,746 | A | 1/1991 | Barbier et al. |
| 5,175,186 | A | 12/1992 | Barbier et al. |
| 5,246,960 | A | 9/1993 | Barbier et al. |
| 5,399,720 | A | 3/1995 | Karpf et al. |
| 6,004,996 | A | 12/1999 | Shah et al. |

FOREIGN PATENT DOCUMENTS

| | | |
|---|---|---|
| EP | 0 189 577 | 12/1989 |
| EP | 0 185 359 | 12/1991 |
| EP | 0 572 863 | 5/1993 |
| EP | 639573 | 7/1994 |
| EP | 0 524 495 | 10/1996 |
| EP | 0 443 449 | 5/1997 |
| WO | WO98/25920 | 6/1998 |
| WO | WO 99/34786 | 7/1999 |
| WO | WO 00/09122 | 2/2000 |
| WO | WO 00/09123 | 2/2000 |
| WO | WO00/46196 A1 | 8/2000 |
| WO | WO 00/58293 | 10/2000 |
| WO | WO01/51466 | 7/2001 |
| WO | WO02/10169 | 2/2002 |
| WO | WO02/051844 | 7/2002 |
| WO | WO02/072584 | 9/2002 |
| WO | WO03/037327 | 5/2003 |
| WO | WO 03/064423 | 8/2003 |
| WO | WO 2005000849 | 1/2005 |

OTHER PUBLICATIONS

Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.
H. Ishii et. al, Chem. Pharm. Bull. 1974, 22 (9), 1981.
T. Hino et. al, Chem. Pharm. Bull. 1990, 38 (1), 59.
M. Tani et. al, Heterocycles 1992, 34 (12), 2349.
L.I. Kruse, et. al, Journal of Organic Chemistry 1984, 49 (25), 4761.
T.J. Tewson et. al, J. Org. Chem. 2002, 67, 5164.
F. Zaragoza, et. al, J. Med. Chem. 2004, 47, 2833.
Amos B. Smith III et. al, J. Am. Chem. Soc. 1989, 111 (15), 5761-5768.
Takahashi, K, Tokita, S., Kotani, H. (2003) J. Pharmacol. Exp. Therapeutics 307, 213-218.
Cheng, Y, Prusoff, WH (1973) Biochem Pharmacol 22, 3099-3108.
M. Tordeux et. al, J. Fluorine Chem. 20, 301 (1982).
J. Org. Chem. 1974, 39, 3580.

*Primary Examiner*—James O Wilson
*Assistant Examiner*—Brian McDowell
(74) *Attorney, Agent, or Firm*—George W. Johnston; Dennis P. Tramaloni; Samuel H. Megerditchian

(57) ABSTRACT

The present invention relates to compounds of formula I

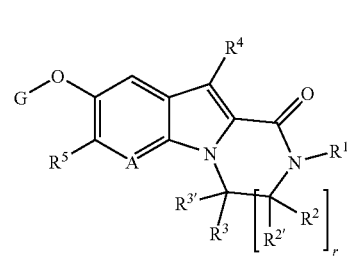

wherein A, G, r and $R^1$ to $R^5$ are as defined in the description and claims, and pharmaceutically acceptable salts thereof. The compounds are useful for the treatment and/or prevention of diseases which are associated with the modulation of H3 receptors such as, for example, diabetes mellitus.

20 Claims, No Drawings

TRICYCLIC AMIDE DERIVATIVES AS MODULATORS OF H3 RECEPTORS

PRIORITY TO RELATED APPLICATIONS

This application is a division of U.S. application Ser. No. 11/605,899, filed Nov. 29, 2006, now pending, which claims the benefit of European Application No. 05111879.2, filed Dec. 9, 2005, which is hereby incorporated by reference in its entirety.

FIELD OF THE INVENTION

The present invention is concerned with novel tricyclic amide derivatives, their manufacture, pharmaceutical compositions containing them and their use as medicaments. The active compounds of the present invention are useful in treating obesity and other disorders.

In particular, the present invention relates to compounds of the general formula

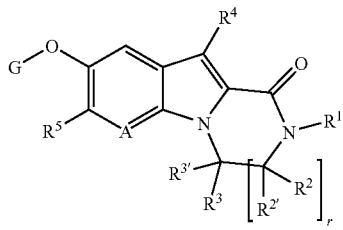

and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

Therefore, there is a need for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In an embodiment of the present invention, provided is a compound of formula I:

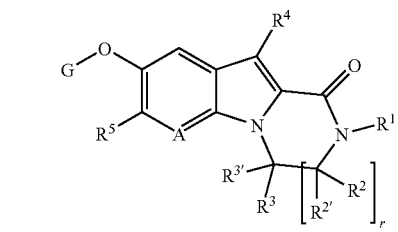

wherein:
A is C or N;
r is 1 or 2;
R$^1$ is selected from the group consisting of hydrogen, lower alkyl,
lower hydroxyalkyl, lower alkoxyalkyl,
lower halogenalkyl, lower hydroxyhalogenalkyl, lower alkanoyl,
lower alkylsulfonyl, lower phenylsulfonyl,
lower cycloalkylalkyl,
lower phenylalkyl, wherein the phenyl ring may be unsubstituted or substituted with one or two groups independently selected from lower alkyl, cyano, halogen, lower halogenalkyl, lower alkoxy and lower hydroxyalkyl,
lower heteroarylalkyl, wherein the heteroaryl ring may be unsubstituted or substituted with one or two groups independently selected from lower alkyl, halogen, phenyl, lower alkoxy and lower hydroxyalkyl,
lower heterocyclylalkyl, wherein the heterocyclyl ring may be unsubstituted or substituted with one or two groups independently selected from lower alkyl, halogen, phenyl, lower alkoxy and lower hydroxyalkyl, and
—$CH_2$—CO—$NR^{14}R^{15}$, wherein
$R^{14}$ and $R^{15}$ independently from each other are selected from the group hydrogen, lower alkyl and phenyl unsubstituted or substituted with one or two groups independently selected from lower alkyl, halogen, lower halogenoalkoxy and lower hydroxyalkyl,
or $R^{14}$ and $R^{15}$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group,
said heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl;
$R^2$, $R^{2'}$, $R^3$ and $R^{3'}$ independently from each other are selected from the group consisting of hydrogen, lower alkyl, lower hydroxyalkyl and lower alkoxyalkyl;
$R^4$ is selected from the group consisting of hydrogen and halogen;
$R^5$ is hydrogen or halogen;
G is a group selected from

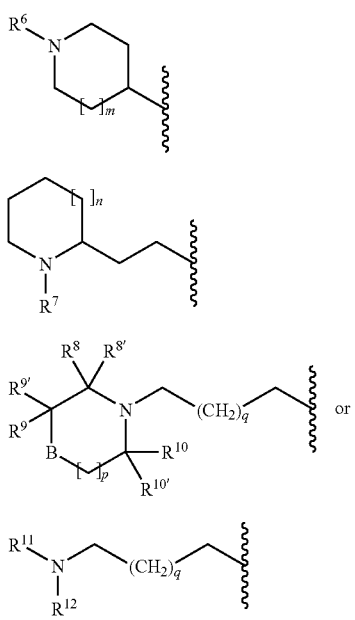

G1

G2

G3

G4 wherein
m is 0, 1 or 2;
$R^6$ is selected from lower alkyl, cycloalkyl, lower cycloalkylalkyl and lower phenylalkyl;
n is 0, 1 or 2;
$R^7$ is lower alkyl;
B is selected from $CR^{13}R^{13'}$, O and S;
$R^8$, $R^{8'}$, $R^9$, $R^{9'}$, $R^{10}$, $R^{10'}$, $R^{13}$ and $R^{13'}$ independently from each other are selected from the group consisting of hydrogen, lower alkyl, hydroxy, halogen and dialkylamino, or
$R^9$ and $R^{13}$ together form a double bond;
p is 0, 1 or 2;
q is 0, 1 or 2;
$R^{11}$ is lower alkyl;
$R^{12}$ is lower alkyl;
and pharmaceutically acceptable salts thereof.

In another embodiment of the present invention, provided is a process for the manufacture of a compound according to formula I, comprising the steps of:

reacting a compound of the formula II

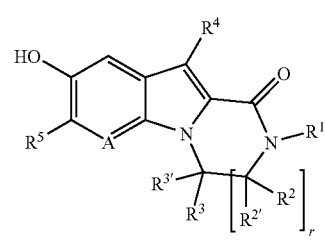

II wherein A, r and $R^1$ to $R^5$ are as defined above, with an alcohol of the formula III

HO-G    III wherein G is as defined herein before, in the presence of a trialkylphosphine or triphenylphosphine and of an azo compound to obtain the compound of the formula IA

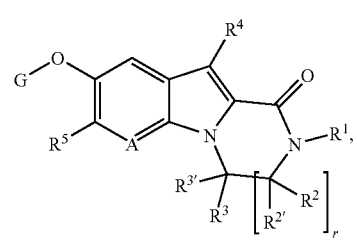

IA wherein $R^1$ is hydrogen, and optionally transferring into a compound of formula IB

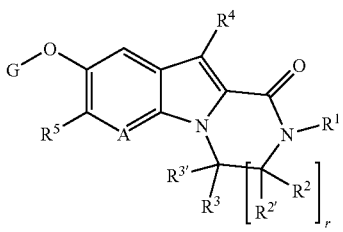

wherein R¹ is a group as defined above other than hydrogen, and optionally, converting the compound obtained into a pharmaceutically acceptable acid addition salt.

In a further embodiment of the present invention, provided is a pharmaceutical composition, comprising a therapeutically effective amount of a compound according to formula I as well as a pharmaceutically acceptable carrier and/or adjuvant.

In a yet another embodiment of the present invention, provided is a method for the treatment of diseases which are associated with the modulation of H3 receptors, comprising the step of administering a therapeutically active amount of a compound according to formula I to a human being or animal in need thereof.

In a still further embodiment of the present invention, provided is a method for the treatment of obesity in a human being or animal, comprising the step of administering a therapeutically effective amount of a compound according to formula I in combination or association with a therapeutically effective amount of a compound selected from the group consisting of a lipase inhibitor, an anorectic agent, a selective serotonin reuptake inhibitor, and an agent that stimulates metabolism of body fat, to said human being or animal in need thereof.

In a yet still another embodiment of the present invention, provided is a method of treatment of type II diabetes in a human being or animal, comprising the step of administering a therapeutically effective amount of a compound according to formula I in combination or association with a therapeutically effective amount of an anti-diabetic agent to said human being or animal in need thereof.

DETAILED DESCRIPTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl and cyclobutyl.

The term "lower cycloalkylalkyl" or "$C_{3-7}$-cycloalkyl-$C_{1-8}$-alkyl" refers to lower alkyl groups as defined above wherein at least one of the hydrogen atoms of the lower alkyl group is replaced by cycloalkyl. A preferred example is cyclopropylmethyl.

The term "alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "$C_{1-8}$-alkoxy-$C_{1-8}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "halogen" refers to fluorine, chlorine, bromine and iodine, with fluorine, chlorine and bromine being preferred.

The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, fluoromethyl and chloromethyl, with trifluoroethyl being especially preferred.

The term "lower hydroxyhalogenalkyl" or "hydroxyhalogen-$C_{1-8}$-alkyl" refers to lower halogenalkyl groups as defined above wherein at least one additional hydrogen atom of the lower alkyl group is replaced by a hydroxy group. A preferred example for a lower hydroxyhalogenalkyl group is 4,4,4-trifluoro-3-hydroxy-butyl.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "carbamoyl" refers to the group —CO—NH$_2$.

The term "lower phenylalkyl" or "phenyl-$C_{1-8}$-alkyl" to lower alkyl groups as defined above wherein at least one of the hydrogen atoms of the lower alkyl group is replaced by a phenyl group. Preferred lower phenylalkyl groups are benzyl or phenethyl.

The term "heteroaryl" refers to an aromatic 5- or 6-membered ring which can comprise one, two or three atoms selected from nitrogen, oxygen and/or sulphur. Examples of heteroaryl groups are e.g. furyl, pyridyl, pyrazinyl, pyrimidinyl, pyridazinyl, thienyl, isoxazolyl, thiazolyl, isothiazolyl, oxazolyl, imidazolyl, or pyrrolyl. Especially preferred are pyridyl, thiazolyl and oxazolyl.

The term "lower heteroarylalkyl" or "heteroaryl-$C_{1-8}$-alkyl" refers to lower alkyl groups as defined above wherein at least one of the hydrogen atoms of the lower alkyl group is replaced by a heteroaryl group as defined above.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl. A preferred heterocyclyl group is piperidinyl.

The term "lower heterocyclylalkyl" or "heterocyclyl-$C_{1-8}$-alkyl" refers to lower alkyl groups as defined above wherein at least one of the hydrogen atoms of the lower alkyl group is replaced by a heterocyclyl group as defined above.

The term "form a 4-, 5-, 6- or 7-membered heterocyclic ring optionally containing a further heteroatom selected from nitrogen, oxygen or sulfur" refers to a N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered heterocyclic ring containing a sulfinyl group or a sulfonyl group" means a N-heterocyclic ring that contains a —S(O)— group or a —SO$_2$— group, for example 1-oxothiomorpholinyl or 1,1-dioxothiomorpholinyl. The heterocyclic ring may be unsubstituted or substituted by one, two or three groups independently selected from lower alkyl, lower alkoxy and oxo. The heterocyclic ring may also be condensed with a phenyl ring, said phenyl ring being unsubstituted or substituted by one, two or three groups independently selected from lower alkyl, lower alkoxy and halogen. An example for such a condensed heterocyclic ring is 3,4-dihydro-1H-isoquinoline.

The term "oxo" means that a C-atom of the heterocyclic ring may be substituted by =O, thus meaning that the heterocyclic ring may contain one or more carbonyl (—CO—) groups.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers".

Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

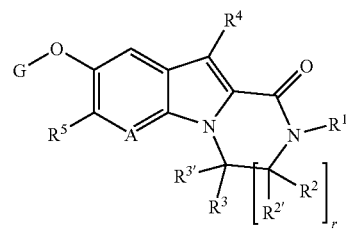

I wherein
  A is C or N;
  r is 1 or 2;
  $R^1$ is selected from the group consisting of hydrogen,
    lower alkyl,
    lower hydroxyalkyl, lower alkoxyalkyl,
    lower halogenalkyl, lower hydroxyhalogenalkyl,
    lower alkanoyl,
    lower alkylsulfonyl, lower phenylsulfonyl,
    lower cycloalkylalkyl,
    lower phenylalkyl, wherein the phenyl ring may be unsubstituted or substituted with one or two groups independently selected from lower alkyl, cyano, halogen, lower halogenalkyl, lower alkoxy and lower hydroxyalkyl,
    lower heteroarylalkyl, wherein the heteroaryl ring may be unsubstituted or substituted with one or two groups independently selected from lower alkyl, halogen, phenyl, lower alkoxy and lower hydroxyalkyl, lower heterocyclylalkyl, wherein the heterocyclyl ring may be unsubstituted or substituted with one or two groups independently selected from lower alkyl, halogen, phenyl, lower alkoxy and lower hydroxyalkyl, and —CH$_2$—CO—NR$^{14}$R$^{15}$, wherein R$^{14}$ and R$^{15}$ independently from each other are selected from the group hydrogen, lower alkyl and phenyl unsubstituted or substituted with one or two groups independently selected from lower alkyl, halogen, lower halogenoalkoxy and lower hydroxyalkyl, or R$^{14}$ and R$^{15}$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl;

R$^2$, R$^{2'}$, R$^3$ and R$^{3'}$ independently from each other are selected from the group consisting of hydrogen, lower alkyl, lower hydroxyalkyl and lower alkoxyalkyl;

R$^4$ is selected from the group consisting of hydrogen and halogen;

R$^5$ is hydrogen or halogen;

G is a group selected from

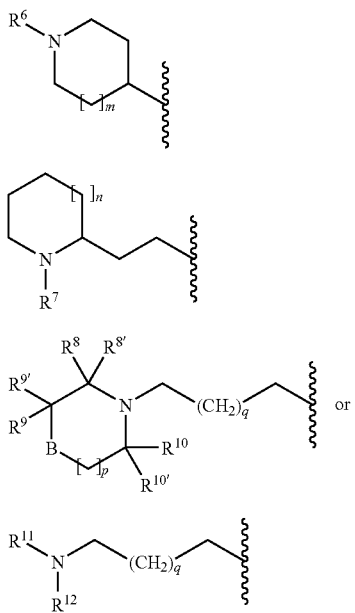

wherein m is 0, 1 or 2;

R$^6$ is selected from lower alkyl, cycloalkyl, lower cycloalkylalkyl and lower phenylalkyl;

n is 0, 1 or 2;

R$^7$ is lower alkyl;

B is selected from CR$^{13}$R$^{13'}$, O and S;

R$^8$, R$^{8'}$, R$^9$, R$^{9'}$, R$^{10}$, R$^{10'}$, R$^{13}$ and R$^{13'}$ independently from each other are selected from the group consisting of hydrogen, lower alkyl, hydroxy, halogen and dialkylamino, or R$^9$ and R$^{13}$ together form a double bond;

p is 0, 1 or 2;

q is 0, 1 or 2;

R$^{11}$ is lower alkyl;

R$^{12}$ is lower alkyl;

and pharmaceutically acceptable salts thereof.

Preferred compounds of formula I of the present invention are compounds of formula I, wherein R$^1$ is selected from the group consisting of hydrogen, lower alkyl, lower hydroxyalkyl, lower alkoxyalkyl, lower halogenalkyl, lower hydroxyhalogenalkyl, lower alkylcarbonyl, lower alkylsulfonyl, lower phenylsulfonyl, lower cycloalkylalkyl, lower phenylalkyl, wherein the phenyl ring may be unsubstituted or substituted with one or two groups independently selected from lower alkyl, cyano, halogen, lower halogenalkyl, lower alkoxy and lower hydroxyalkyl, and lower heteroarylalkyl, wherein the heteroaryl ring may be unsubstituted or substituted with one or two groups independently selected from lower alkyl, halogen, phenyl, lower alkoxy and lower hydroxyalkyl.

Within this group, those compounds of formula I are preferred, wherein R$^1$ is selected from the group consisting of hydrogen, lower alkyl, lower hydroxyalkyl, lower alkoxyalkyl, lower halogenalkyl, lower hydroxyhalogenalkyl, lower alkanoyl, lower alkylsulfonyl, lower phenylsulfonyl and lower cycloalkylalkyl.

Compounds of formula I according to the invention are also preferred, wherein R$^1$ is lower phenylalkyl, wherein the phenyl ring may be unsubstituted or substituted with one or two groups independently selected from lower alkyl, cyano, halogen, lower halogenalkyl, lower alkoxy and lower hydroxyalkyl. Especially preferred are those compounds, wherein the phenyl ring is substituted with a cyano group.

Further preferred compounds of formula I according to the invention are those, wherein R$^1$ is lower heteroarylalkyl, wherein the heteroaryl ring may be unsubstituted or substituted with one or two groups independently selected from lower alkyl, halogen, phenyl, lower alkoxy and lower hydroxyalkyl.

Also preferred are compounds of formula I according to the present invention, wherein R$^1$ is —CH$_2$—CO—NR$^{14}$R$^{15}$, wherein R$^{14}$ and R$^{15}$ independently from each other are selected from the group hydrogen, lower alkyl and phenyl unsubstituted or substituted with one or two groups independently selected from lower alkyl, lower halogenoalkoxy and lower hydroxyalkyl, or R$^{14}$ and R$^{15}$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl.

Furthermore, those compounds of formula I are preferred, wherein at least one of R$^{14}$ and R$^{15}$ is lower alkyl or R$^{14}$ and R$^{15}$ are both lower alkyl. Also preferred are those compounds, wherein R$^{14}$ and R$^{15}$ together with the nitrogen atom to which they are attached form a morpholine or piperidine ring which is optionally substituted by lower alkyl, halogen, halogenalkyl, hydroxy, lower hydroxyalkyl, lower alkoxy, oxo, phenyl, benzyl, pyridyl and carbamoyl.

Especially preferred are compounds of formula I of the invention, wherein $R^2$, $R^{2'}$, $R^3$ and $R^{3'}$ are hydrogen.

Further preferred compounds of formula I according to the invention are those, wherein one of $R^2$, $R^{2'}$, $R^3$ and $R^{3'}$ is selected from the group consisting of lower alkyl, lower hydroxyalkyl and lower alkoxyalkyl.

$R^4$ signifies hydrogen or halogen. Preferably, $R^4$ is selected from the group consisting of hydrogen, chloro, bromo and iodo. Especially preferred are those compounds of formula I, wherein $R^4$ is hydrogen.

$R^5$ signifies hydrogen or halogen. Preferably, $R^5$ is selected from the group consisting of hydrogen, chloro and bromo. Especially preferred are the compounds of formula I, wherein $R^5$ is hydrogen.

Furthermore, compounds of formula I according to the invention are preferred, wherein r is 1.

However, those compounds of formula I, wherein r signifies 2, are also preferred.

In addition, compounds of formula I according to the present invention are preferred, wherein A signifies C (a carbon atom).

Compounds of formula I according to the invention are also preferred, wherein A signifies N (a nitrogen atom).

Further preferred are compounds of formula I according to any one of claims 1 to 13, wherein G signifies

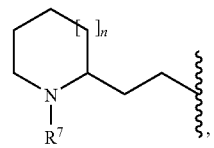

wherein m is 0, 1 or 2, and $R^6$ is selected from the group consisting of lower alkyl, cycloalkyl, lower cycloalkylalkyl and lower phenylalkyl.

Within this group, those compounds of formula I are more preferred, wherein $R^6$ is lower alkyl, with those compounds, wherein $R^6$ is isopropyl, being most preferred.

Further preferred compounds of formula I according to the present invention are those compounds, wherein G signifies

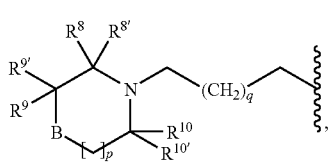

wherein p is 0, 1 or 2; q is 0, 1 or 2; B is selected from $CR^{13}R^{13'}$, O and S; and $R^8$, $R^{8'}$, $R^9$, $R^{9'}$, $R^{10}$, $R^{10'}$, $R^{13}$ and $R^{13'}$ independently from each other are selected from the group consisting of hydrogen, lower alkyl, hydroxy, halogen and dialkylamino, or $R^9$ and $R^{13}$ together form a double bond.

Within this group, those compounds of formula I are more preferred, wherein p is 0 or 1, q is 0, B is $CR^{13}R^{13'}$ and $R^8$, $R^{8'}$, $R^9$, $R^{9'}$, $R^{10}$, $R^{10'}$, $R^{13}$ and $R^{13'}$ independently from each other are selected from the group consisting of hydrogen, lower alkyl, hydroxy, halogen and dialkylamino.

Also preferred are compounds of formula I, wherein G signifies

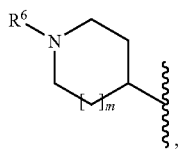

wherein n is 0, 1 or 2; and $R^7$ is lower alkyl.

Compounds of formula I according to the present invention, wherein G signifies

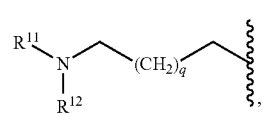

wherein q is 0, 1 or 2, $R^{11}$ is lower alkyl and $R^{12}$ is lower alkyl, are also preferred.

Examples of preferred compounds of formula I are the following:

8-(1-isopropyl-piperidin-4-yloxy)-3,4-dihydro-2H-pyrazino[1,2-a]indol-1-one, 8-(3-piperidin-1-yl-propoxy)-3,4-dihydro-2H-pyrazino[1,2-a]indol-1-one, 8-(1-cyclopropylmethyl-piperidin-4-yloxy)-3,4-dihydro-2H-pyrazino[1,2-a]indol-1-one, 8-[3-((R)-3-hydroxy-pyrrolidin-1-yl)-propoxy]-3,4-dihydro-2H-pyrazino[1,2-a]indol-1-one, 8-[3-((R)-2-methyl-pyrrolidin-1-yl)-propoxy]-3,4-dihydro-2H-pyrazino[1,2-a]indol-1-one, 8-[3-((S)-2-methyl-pyrrolidin-1-yl)-propoxy]-3,4-dihydro-2H-pyrazino[1,2-a]indol-1-one, 8-[3-((2S,5S)-2,5-dimethyl-pyrrolidin-1-yl)-propoxy]-3,4-dihydro-2H-pyrazino[1,2-a]indol-1-one, (R)-8-(1-isopropyl-piperidin-4-yloxy)-4-methyl-3,4-dihydro-2H-pyrazino[1,2-a]indol-1-one, (R)-4-methyl-8-(3-piperidin-1-yl-propoxy)-3,4-dihydro-2H-pyrazino[1,2-a]indol-1-one, (R)-8-[3-((R)-3-hydroxy-pyrrolidin-1-yl)-propoxy]-4-methyl-3,4-dihydro-2H-pyrazino[1,2a]indol-1-one, (S)-8-(1-isopropyl-piperidin-4-yloxy)-4-methyl-3,4-dihydro-2H-pyrazino[1,2-a]indol-1-one, (S)-4-hydroxymethyl-8-(1-isopropyl-piperidin-4-yloxy)-3,4-dihydro-2H-pyrazino[1,2-a]indol-1-one, (S)-8-(1-isopropyl-piperidin-4-yloxy)-3-methyl-3,4-dihydro-2H-pyrazino[1,2-a]indol-1-one, (R)-8-(1-isopropyl-piperidin-4-yloxy)-3-methyl-3,4-dihydro-2H-pyrazino[1,2-a]indol-1-one, 9-(1-isopropyl-piperidin-4-yloxy)-2,3,4,5-tetrahydro-[1,4]diazepino[1,2-a]indol-1-one, 9-(3-pyrrolidin-1-yl-propoxy)-2,3,4,5-tetrahydro-[1,4]diazepino[1,2-a]indol-1-one, 2-cyclopropylmethyl-8-(1-isopropyl-piperidin-4-yloxy)-3,4-dihydro-2H-pyrazino[1,2-a]indol-1-one, 8-(1-isopropyl-piperidin-4-yloxy)-2-(2-methoxy-ethyl)-3,4-dihydro-2H-pyrazino[1,2-a]indol-1-one, 8-(1-isopropyl-piperidin-4-yloxy)-2-(2,2,2-trifluoro-ethyl)-3,4-dihydro-2H-pyrazino[1,2-a]indol-1-one, 8-(1-isopropyl-piperidin-4-yloxy)-2-methyl-3,4-dihydro-2H-pyrazino[1,2-a]indol-1-one,
2-ethyl-8-(1-isopropyl-piperidin-4-yloxy)-3,4-dihydro-2H-pyrazino[1,2-a]indol-1-one,
2-isopropyl-8-(1-isopropyl-piperidin-4-yloxy)-3,4-dihydro-2H-pyrazino[1,2-a]indol-1-one,
(R)-2-cyclopropylmethyl-8-(1-isopropyl-piperidin-4-yloxy)-4-methyl-3,4-dihydro-2H-pyrazino[1,2-a]indol-1-one,
(R)-8-(1-isopropyl-piperidin-4-yloxy)-2-(2-methoxy-ethyl)-4-methyl-3,4-dihydro-2H-pyrazino[1,2-a]indol-1-one,
(R)-8-(1-isopropyl-piperidin-4-yloxy)-2,4-dimethyl-3,4-dihydro-2H-pyrazino[1,2-a]indol-1-one,
(R)-8-(1-isopropyl-piperidin-4-yloxy)-4-methyl-2-(2,2,2-trifluoro-ethyl)-3,4-dihydro-2H-pyrazino[1,2-a]indol-1-one,
2-ethyl-8-(1-isopropyl-piperidin-4-yloxy)-4-methyl-3,4-dihydro-2H-pyrazino[1,2-a]indol-1-one,
(S)-2-cyclopropylmethyl-8-(1-isopropyl-piperidin-4-yloxy)-4-methyl-3,4-dihydro-2H-pyrazino[1,2-a]indol-1-one,
(S)-8-(1-isopropyl-piperidin-4-yloxy)-2-(2-methoxy-ethyl)-4-methyl-3,4-dihydro-2H-pyrazino[1,2-a]indol-1-one,
(S)-2-cyclopropylmethyl-8-(1-isopropyl-piperidin-4-yloxy)-3-methyl-3,4-dihydro-2H-pyrazino[1,2-a]indol-1-one,
(S)-8-(1-isopropyl-piperidin-4-yloxy)-2-(2-methoxy-ethyl)-3-methyl-3,4-dihydro-2H-pyrazino[1,2-a]indol-1-one,
(R)-2-cyclopropylmethyl-8-(1-isopropyl-piperidin-4-yloxy)-3-methyl-3,4-dihydro-2H-pyrazino[1,2-a]indol-1-one,
(R)-8-(1-isopropyl-piperidin-4-yloxy)-2-(2-methoxy-ethyl)-3-methyl-3,4-dihydro-2H-pyrazino[1,2-a]indol-1-one,
2-[8-(1-isopropyl-piperidin-4-yloxy)-1-oxo-3,4-dihydro-1H-pyrazino[1,2-a]indol-2-yl]-acetamide,
2-[8-(1-isopropyl-piperidin-4-yloxy)-1-oxo-3,4-dihydro-1H-pyrazino[1,2-a]indol-2-yl]-N-methyl-acetamide,
2-[8-(1-isopropyl-piperidin-4-yloxy)-1-oxo-3,4-dihydro-1H-pyrazino[1,2-a]indol-2-yl]-N,N-dimethyl-acetamide,
8-(1-isopropyl-piperidin-4-yloxy)-2-(2-morpholin-4-yl-2-oxo-ethyl)-3,4-dihydro-2H-pyrazino[1,2-a]indol-1-one,
N-isopropyl-2-[8-(1-isopropyl-piperidin-4-yloxy)-1-oxo-3,4-dihydro-1H-pyrazino[1,2-a]indol-2-yl]-acetamide,
N,N-diisopropyl-2-[8-(1-isopropyl-piperidin-4-yloxy)-1-oxo-3,4-dihydro-1H-pyrazino[1,2-a]indol-2-yl]-acetamide,
2-[8-(1-isopropyl-piperidin-4-yloxy)-1-oxo-3,4-dihydro-1H-pyrazino[1,2-a]indol-2-yl]-N-phenyl-acetamide,
2-benzyl-8-(1-isopropyl-piperidin-4-yloxy)-3,4-dihydro-2H-pyrazino[1,2a]indol-1-one,
8-(1-isopropyl-piperidin-4-yloxy)-2-(2-trifluoromethyl-benzyl)-3,4-dihydro-2H-pyrazino[1,2-a]indol-1-one,
8-(1-isopropyl-piperidin-4-yloxy)-2-(3-trifluoromethyl-benzyl)-3,4-dihydro-2H-pyrazino[1,2-a]indol-1-one,
8-(1-isopropyl-piperidin-4-yloxy)-2-(4-trifluoromethyl-benzyl)-3,4-dihydro-2H-pyrazino[1,2-a]indol-1-one,
8-(1-isopropyl-piperidin-4-yloxy)-2-(2-methoxy-benzyl)-3,4-dihydro-2H-pyrazino[1,2-a]indol-1-one,
8-(1-isopropyl-piperidin-4-yloxy)-2-(3-methoxy-benzyl)-3,4-dihydro-2H-pyrazino[1,2-a]indol-1-one,
8-(1-isopropyl-piperidin-4-yloxy)-2-(4-methoxy-benzyl)-3,4-dihydro-2H-pyrazino[1,2-a]indol-1-one,
2-(2-fluoro-benzyl)-8-(1-isopropyl-piperidin-4-yloxy)-3,4-dihydro-2H-pyrazino[1,2-a]indol-1-one,
2-(3-fluoro-benzyl)-8-(1-isopropyl-piperidin-4-yloxy)-3,4-dihydro-2H-pyrazino[1,2-a]indol-1-one,
2-(4-fluoro-benzyl)-8-(1-isopropyl-piperidin-4-yloxy)-3,4-dihydro-2H-pyrazino[1,2-a]indol-1-one,
2-[8-(1-isopropyl-piperidin-4-yloxy)-1-oxo-3,4-dihydro-1H-pyrazino[1,2-a]indol-2-ylmethyl]-benzonitrile,
3-[8-(1-isopropyl-piperidin-4-yloxy)-1-oxo-3,4-dihydro-1H-pyrazino[1,2-a]indol-2-ylmethyl]-benzonitrile,
4-[8-(1-isopropyl-piperidin-4-yloxy)-1-oxo-3,4-dihydro-1H-pyrazino[1,2-a]indol-2-ylmethyl]-benzonitrile,
8-(1-isopropyl-piperidin-4-yloxy)-2-pyridin-2-ylmethyl-3,4-dihydro-2H-pyrazino[1,2-a]indol-1-one,
8-(1-isopropyl-piperidin-4-yloxy)-2-pyridin-3-ylmethyl-3,4-dihydro-2H-pyrazino[1,2-a]indol-1-one,
8-(1-isopropyl-piperidin-4-yloxy)-2-pyridin-4-ylmethyl-3,4-dihydro-2H-pyrazino[1,2-a]indol-1-one,
8-(1-isopropyl-piperidin-4-yloxy)-2-(1-phenyl-ethyl)-3,4-dihydro-2H-pyrazino[1,2-a]indol-1-one,
2-(3-hydroxy-propyl)-8-(1-isopropyl-piperidin-4-yloxy)-3,4-dihydro-2H-pyrazino[1,2-a]indol-1-one,
2-(2-hydroxy-ethyl)-8-(1-isopropyl-piperidin-4-yloxy)-3,4-dihydro-2H-pyrazino[1,2-a]indol-1-one,
(R)-2-benzyl-8-(1-isopropyl-piperidin-4-yloxy)-4-methyl-3,4-dihydro-2H-pyrazino[1,2-a]indol-1-one,
(R)-8-(1-isopropyl-piperidin-4-yloxy)-4-methyl-2-pyridin-2-ylmethyl-3,4-dihydro-2H-pyrazino[1,2-a]indol-1-one,
(R)-8-(1-isopropyl-piperidin-4-yloxy)-4-methyl-2-pyridin-3-ylmethyl-3,4-dihydro-2H-pyrazino[1,2-a]indol-1-one,
(R)-8-(1-isopropyl-piperidin-4-yloxy)-4-methyl-2-pyridin-4-ylmethyl-3,4-dihydro-2H-pyrazino[1,2-a]indol-1-one,
(R)-8-(1-isopropyl-piperidin-4-yloxy)-4-methyl-2-(2-methyl-thiazol-4-ylmethyl)-3,4-dihydro-2H-pyrazino[1,2-a]indol-1-one,
(R)-8-(1-isopropyl-piperidin-4-yloxy)-4-methyl-2-(5-methyl-2-phenyl-oxazol-4-ylmethyl)-3,4-dihydro-2H-pyrazino[1,2-a]indol-1-one,
(R)-8-(1-isopropyl-piperidin-4-yloxy)-4-methyl-2-(5-phenyl-[1,2,4]oxadiazol-3-ylmethyl)-3,4-dihydro-2H-pyrazino[1,2-a]indol-1-one,
(R)-2-(3,5-dimethyl-isoxazol-4-ylmethyl)-8-(1-isopropyl-piperidin-4-yloxy)-4-methyl-3,4-dihydro-2H-pyrazino[1,2-a]indol-1-one,
(R)-8-(1-isopropyl-piperidin-4-yloxy)-4-methyl-2-(5-methyl-3-phenyl-isoxazol-4-ylmethyl)-3,4-dihydro-2H-pyrazino[1,2-a]indol-1-one,
(R)-8-(1-isopropyl-piperidin-4-yloxy)-4-methyl-2-(5-methyl-isoxazol-3-ylmethyl)-3,4-dihydro-2H-pyrazino[1,2-a]indol-1-one,
(R)-2-(3-hydroxy-propyl)-8-(1-isopropyl-piperidin-4-yloxy)-4-methyl-3,4-dihydro-2H-pyrazino[1,2-a]indol-1-one,
(R)-2-(2-hydroxy-ethyl)-8-(1-isopropyl-piperidin-4-yloxy)-4-methyl-3,4-dihydro-2H-pyrazino[1,2-a]indol-1-one,
(R)-8-(1-isopropyl-piperidin-4-yloxy)-4-methyl-2-((R)-4,4,4-trifluoro-3-hydroxy-butyl)-3,4-dihydro-2H-pyrazino[1,2-a]indol-1-one,
(R)-2-acetyl-8-(1-isopropyl-piperidin-4-yloxy)-4-methyl-3,4-dihydro-2H-pyrazino[1,2-a]indol-1-one,
(R)-2-benzenesulfonyl-8-(1-isopropyl-piperidin-4-yloxy)-4-methyl-3,4-dihydro-2H-pyrazino[1,2-a]indol-1-one,
(S)-2-cyclopropylmethyl-4-hydroxymethyl-8-(1-isopropyl-piperidin-4-yloxy)-3,4-dihydro-2H-pyrazino[1,2-a]indol-1-one,
(S)-2-cyclopropylmethyl-8-(1-isopropyl-piperidin-4-yloxy)-4-methoxymethyl-3,4-dihydro-2H-pyrazino[1,2-a]indol-1-one
(S)-4-hydroxymethyl-8-(1-isopropyl-piperidin-4-yloxy)-2-methyl-3,4-dihydro-2H-pyrazino[1,2-a]indol-1-one, 2-cyclopropylmethyl-9-(1-isopropyl-piperidin-4-yloxy)-2, 3,4,5-tetrahydro-[1,4]diazepino[1,2-a]indol-1-one,
9-(1-isopropyl-piperidin-4-yloxy)-2-(2-methoxy-ethyl)-2,3, 4,5-tetrahydro-[1,4]diazepino[1,2-a]indol-1-one,
2-cyclopropylmethyl-9-(3-pyrrolidin-1-yl-propoxy)-2,3,4, 5-tetrahydro-[1,4]diazepino[1,2-a]indol-1-one,
2-(2-methoxy-ethyl)-9-(3-pyrrolidin-1-yl-propoxy)-2,3,4,5-tetrahydro-[1,4]diazepino[1,2-a]indol-1-one,
(R)-10-chloro-8-(1-isopropyl-piperidin-4-yloxy)-4-methyl-3,4-dihydro-2H-pyrazino[1,2-a]indol-1-one,
(R)-10-bromo-8-(1-isopropyl-piperidin-4-yloxy)-4-methyl-3,4-dihydro-2H-pyrazino[1,2-a]indol-1-one,
7-(1-isopropyl-piperidin-4-yloxy)-3,4-dihydro-2H-2,4a,5-triaza-fluoren-1-one,
7-[3-((S)-2-methyl-pyrrolidin-1-yl)-propoxy]-3,4-dihydro-2H-2,4a,5-triaza-fluoren-1-one,
7-[3-((R)-2-methyl-pyrrolidin-1-yl)-propoxy]-3,4-dihydro-2H-2,4a,5-triaza-fluoren-1-one,
7-[3-((2R,5R)-2,5-dimethyl-pyrrolidin-1-yl)-propoxy]-3,4-dihydro-2H-2,4a,5-triaza-fluoren-1-one,
7-(1-cyclopropylmethyl-piperidin-4-yloxy)-3,4-dihydro-2H-2,4a,5-triaza-fluoren-1-one,
2-cyclopropylmethyl-7-(1-isopropyl-piperidin-4-yloxy)-3,4-dihydro-2H-2,4a,5-triaza-fluoren-1-one,
7-(1-isopropyl-piperidin-4-yloxy)-2-(2-methoxy-ethyl)-3,4-dihydro-2H-2,4a,5-triaza-fluoren-1-one,
7-(1-isopropyl-piperidin-4-yloxy)-2-(2,2,2-trifluoro-ethyl)-3,4-dihydro-2H-2,4a,5-triaza-fluoren-1-one,
7-[3-((S)-2-methyl-pyrrolidin-1-yl)-propoxy]-2-(2,2,2-trifluoro-ethyl)-3,4-dihydro-2H-2,4a,5-triaza-fluoren-1-one,
(R)-7-bromo-8-(1-isopropyl-piperidin-4-yloxy)-4-methyl-3,4-dihydro-2H-pyrazino[1,2-a]indol-1-one,
(R)-7-bromo-2-cyclopropylmethyl-8-(1-isopropyl-piperidin-4-yloxy)-4-methyl-3,4-dihydro-2H-pyrazino[1,2-a]indol-1-one, and pharmaceutically acceptable salts thereof.

Particularly preferred compounds of formula I of the present invention are the following:
8-[3-((R)-2-methyl-pyrrolidin-1-yl)-propoxy]-3,4-dihydro-2H-pyrazino[1,2-a]indol-1-one,
(S)-8-(1-isopropyl-piperidin-4-yloxy)-3-methyl-3,4-dihydro-2H-pyrazino[1,2-a]indol-1-one,
9-(1-isopropyl-piperidin-4-yloxy)-2,3,4,5-tetrahydro-[1,4]diazepino[1,2-a]indol-1-one,
(R)-8-(1-isopropyl-piperidin-4-yloxy)-2-(2-methoxy-ethyl)-4-methyl-3,4-dihydro-2H-pyrazino[1,2-a]indol-1-one,
(R)-2-cyclopropylmethyl-8-(1-isopropyl-piperidin-4-yloxy)-3-methyl-3,4-dihydro-2H-pyrazino[1,2-a]indol-1-one,
3-[8-(1-isopropyl-piperidin-4-yloxy)-1-oxo-3,4-dihydro-1H-pyrazino[1,2-a]indol-2-ylmethyl]-benzonitrile,
4-[8-(1-isopropyl-piperidin-4-yloxy)-1-oxo-3,4-dihydro-1H-pyrazino[1,2-a]indol-2-ylmethyl]-benzonitrile,
7-[3-((S)-2-methyl-pyrrolidin-1-yl)-propoxy]-2-(2,2,2-trifluoro-ethyl)-3,4-dihydro-2H-2,4a,5-triaza-fluoren-1-one, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate.

Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

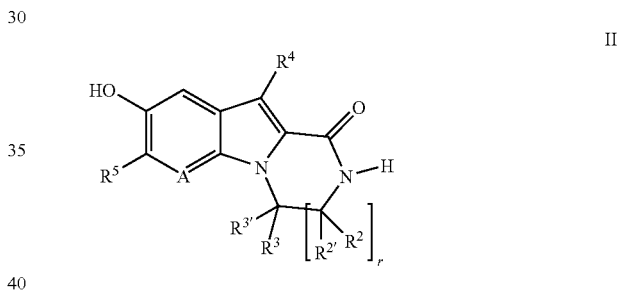

wherein A, r and $R^2$ to $R^5$ are as defined herein before, with an alcohol of the formula III

HO-G    III wherein G is as defined herein before, in the presence of a trialkylphosphine or triphenylphosphine and of an azo compound to obtain the compound of the formula IA

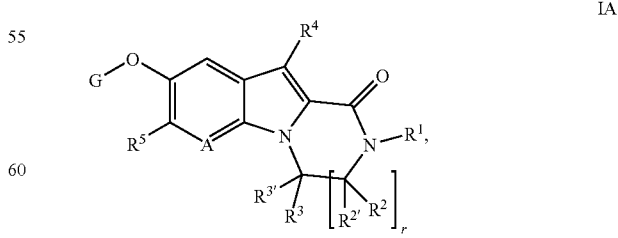

wherein $R^1$ is hydrogen, and optionally transferring into a compound of formula IB

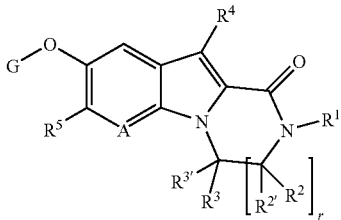

wherein $R^1$ is a group as defined herein before other than hydrogen, and if desired, converting the compound obtained into a pharmaceutically acceptable acid addition salt.

Transferring into a compound of formula IB means treating the compound of formula IA with a suitable base in a suitable solvent under anhydrous conditions (e.g. sodium hydride in DMF) and reacting the intermediate anion with an alkylating or acylating agent $R^1$—X, wherein X signifies a leaving group such as e.g. iodide, bromide, methanesulfonate or chloride, to obtain a compound of formula IB wherein $R^1$ signifies lower alkyl, lower hydroxyalkyl, lower alkoxyalkyl, lower halogenalkyl, lower hydroxyhalogenalkyl, lower cycloalkylalkyl, lower alkylcarbonyl, lower alkylsulfonyl or phenylsulfonyl.

Typical examples of an alkylating or acylating agent $R^3$—X are methyl iodide, benzyl bromide, 2,2,2-trifluoroethyl-methanesulfonate, acetyl chloride or benzenesulfonyl chloride.

In more detail, the compounds of formula I can be manufactured by the methods given below, by the methods given in the examples or by analogous methods. The preparation of compounds of formula I of the present invention may be carried out in sequential or convergent synthetic routes. Syntheses of the invention are shown in the following schemes. The skills required for carrying out the reaction and purification of the resulting products are known to those skilled in the art. The substituents and indices used in the following description of the processes have the significance given herein before unless indicated to the contrary.

Starting materials are either commercially available or can be prepared by methods analogous to the methods given below, by methods described in references cited in the description or in the examples, or by methods known in the art.

Scheme 1

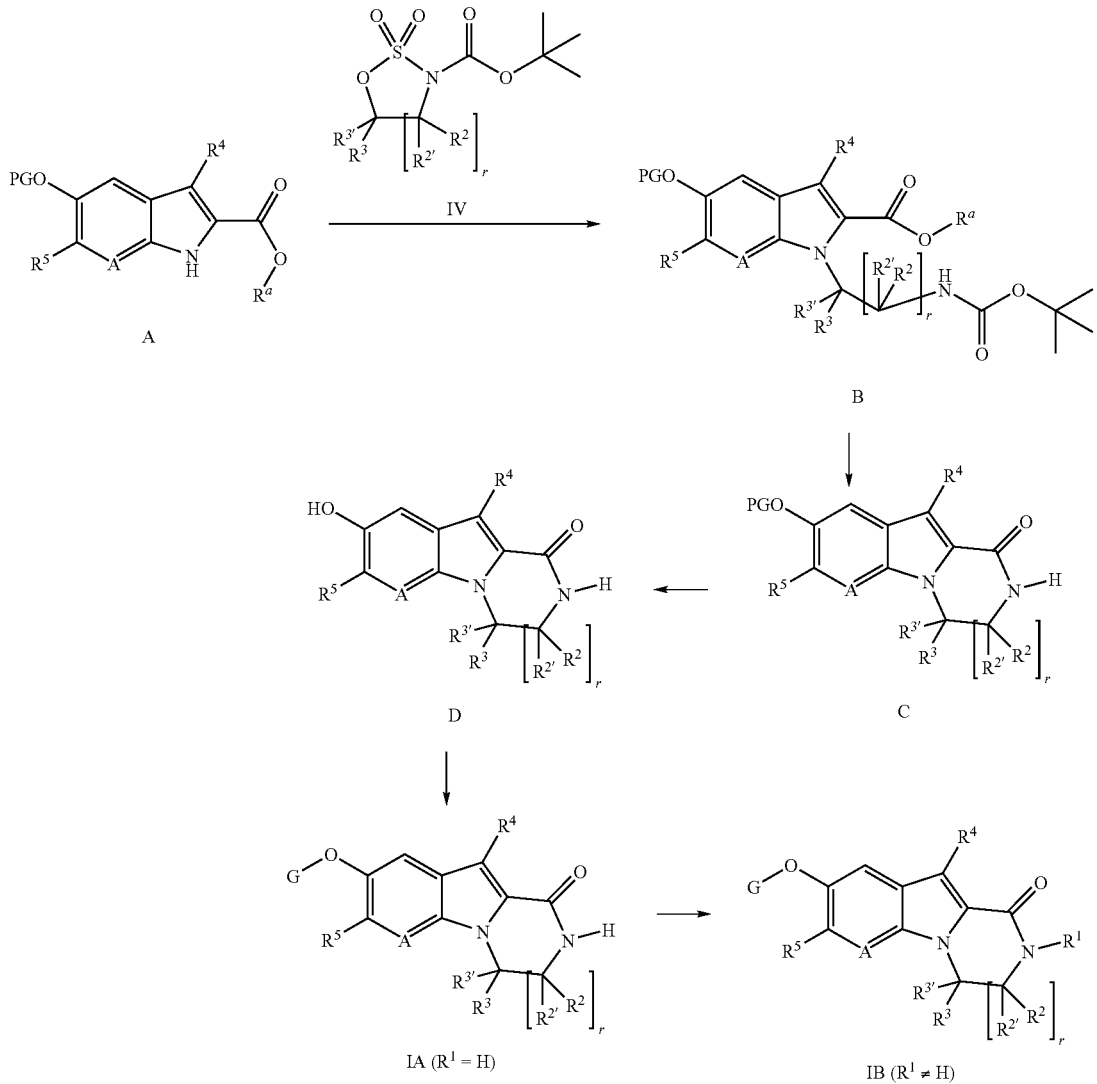

Compounds of the general formula I can be prepared according to scheme 1 by a process where the indole-2-carboxylate of formula A (either commercially available or synthesized employing methods known in the art or described in references, e.g. H. Ishii et. al, Chem. Pharm. Bull. 1974, 22 (9), 1981; T. Hino et. al, Chem. Pharm. Bull. 1990, 38 (1), 59; M. Tani et. al, Heterocycles 1992, 34 (12), 2349; L. I. Kruse, et. al, Journal of Organic Chemistry 1984, 49 (25), 4761; EP639573; WO00/046196A1; WO01/51466) is first reacted with the Boc-sulfamidate IV (prepared as described in literature, e.g. T. J. Tewson et. al, J. Org. Chem. 2002, 67, 5164; WO02/010169; WO02/072584, WO02/051844, WO03/037327) in a suitable solvent (e.g., N,N-dimethylformamide) with a suitable base (e.g., potassium tert-butylate or sodium hydride) to give intermediate B. Removal of the Boc protecting group (Boc means tert-butoxycarbonyl) with a suitable reagent, e.g. trifluoroacetic acid (TFA) in a suitable solvent such as, e.g. dichloromethane and ring closure in the presence of a base (e.g., potassium carbonate) and an appropriate solvent such as, e.g. methanol, yields intermediate C. In cases where a substituent $R^3$ in Boc-sulfamidate IV is attached to the carbon adjacent to the oxygen atom, the stereochemistry of the carbon atom attached to $R^3$ is inverted (>90% e.e.) in this reaction sequence.

The protective group PG is cleaved off by methods known by those skilled in the art and as described in literature (e.g. T. W. Greene and P. G. M. Wuts. Protective Groups in Organic Synthesis. $3^{rd}$ Edition, 1999) to give intermediate D. For example, a benzyl protective group is cleaved off by, e.g. hydrogenolysis using an appropriate catalyst (e.g. palladium on charcoal) in a suitable solvent or solvent mixture (e.g. ethyl acetate, methanol). A methyl group is cleaved off by, e.g. treatment with boron tribromide in an appropriate solvent such as, e.g. dichloromethane. A tert-butyldimethylsilyl protective group is cleaved off by, e.g. treatment with tetra-n-butylammonium fluoride in a suitable solvent such as, e.g. tetrahydrofuran.

Compounds of the general formula IA can be prepared as follows: In case of G I or G II, the resulting phenol is coupled with alcohols of the type HO-G I or HO-G II (either commercially available or accessible by methods described in references or by methods known in the art) applying the so-called "Mitsunobu reaction" which is known to those skilled in the art and widely described (e.g. D. L. Hughes. The Mitsunobu reaction. Organic Reactions (New York) (1992), 42, 335-656). Thereby the phenol intermediate is coupled with alcohols of the type HO-G I or HO-G II using a phosphine like, e.g. tributylphosphine or triphenylphosphine and either an azodicarboxylic acid dialkyl ester like, e.g. diethyl azodicarboxylate (DEAD) or diisopropyl-azodicarboxylate (DIAD) or using N,N,N',N'-tetramethylazodicarboxamide in a solvent commonly used in such transformations like, e.g. tetrahydrofuran (THF), toluene or dichloromethane. In cases where the substituents $R^6$ or $R^7$ are not already present in the alcohols of the type HO-G I or HO-G II, they can be introduced by alkylation of the free amine functionality in compounds of formula IA or IB by employing methods described in references or by methods known in the art such as, e.g. reductive amination (e.g. F. Zaragoza, et. al, J. Med. Chem. 2004, 47, 2833). The before mentioned methodology can be also applied for alcohols of type HO-G III and HO-G IV, or, alternatively, the phenol intermediate is alkylated with α,Ω-dihalo-alkanes such as, e.g. 1-bromo-3-chloropropane under basic conditions (e.g. potassium carbonate) in a suitable solvent (e.g. 2-butanone) and reacting the intermediate chloropropoxy compound with an amine in the presence of a base such as, e.g. potassium carbonate in an appropriate solvent such as, e.g. acetonitrile.

Compounds of formula IB can be obtained through treatment of intermediates of formula IA with a suitable base in a suitable solvent under anhydrous conditions (e.g. sodium hydride in N,N-dimethylformamide) and reacting the intermediate anion with an alkylating or acylating agent $R^1$—X such as, e.g. methyl iodide, benzyl bromide, 2,2,2-trifluoroethyl-methanesulfonate, acetyl chloride or benzenesulfonyl chloride. In those cases $R^1$ signifies a methyl, benzyl, trifluoromethyl, acetyl or a sulfonyl group and X signifies a leaving group such as, e.g. iodide, bromide, methanesulfonate or chloride.

Scheme 2

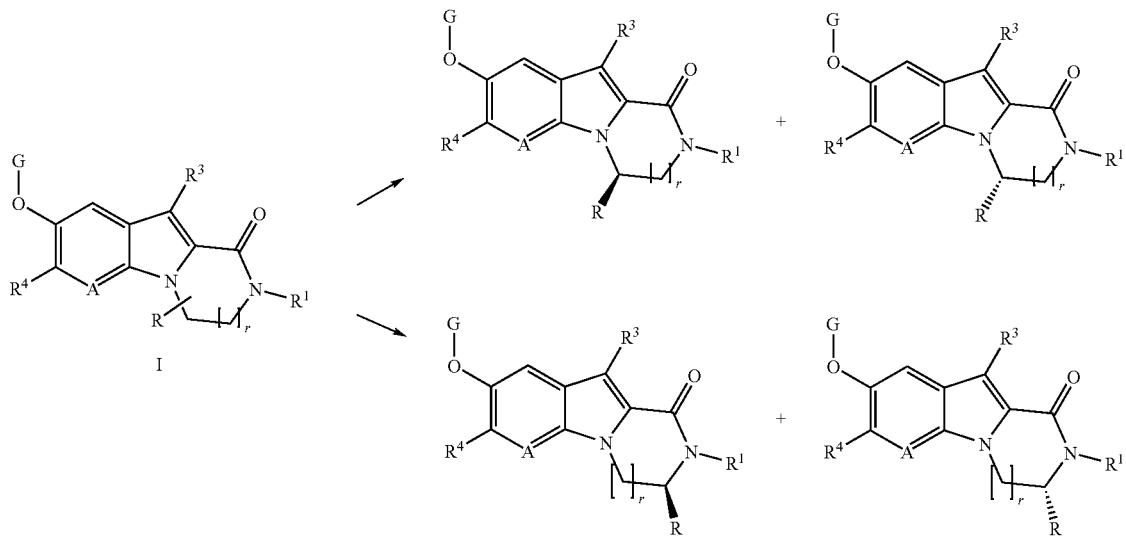

In cases wherein one of $R^2$, $R^{2'}$, $R^3$ and $R^{3'}$ is not hydrogen, the enantiomers of compounds of formula IA and IB can be obtained either by using a chiral sulfamidate IV or by separation of the enantiomers by preparative chiral HPLC or by crystallization with suitable chiral acids, separation of the diastereomeric salts and isolation of the enantiomers from these salts. An alternative access to the enantiomers of compounds of formula IA and IB involves the separation of the enantiomers of the precursor C or D, e.g., by preparative chiral HPLC. Preferably the enantiomers are obtained by using chiral sulfamidate reagents of formula IV.

Compounds of the general formula I can also be synthesized according to scheme 3 from compounds of the general formula IC wherein $R^4$ is hydrogen, which in turn can be obtained according to scheme 1, with an appropriate halogenating agent such as, e.g. N-chloro-, N-bromo- or N-iodosuccinimide in an appropriate solvent such as, e.g. N,N-dimethylformamide. This reaction sequence can be applied to achiral, racemic or chiral compounds of formula IC.

A method for the preparation of compounds of formula A, wherein A signifies N, is shown in scheme 4.

7-Aza-indole-2-carboxylates of formula N can be prepared as depicted in scheme 4 starting from 6-amino-5-bromo-pyridin-3-ol (prepared according to WO98/25920), which can be O-protected with, e.g. a benzyl protective group by using, e.g. benzyl bromide and a base such as, e.g. sodium hydride in an appropriate solvent such as, e.g. N,N-dimethylformamide. PG thus means a hydroxy protecting group, e.g. a benzyl group. Reaction of intermediate E with optionally protected (e.g. with a dimethylhexylsilyl protective group) carbinol derivatives leads to intermediate F. PG' thus means a hydroxy protecting group, e.g. a silyl protecting group such as dimethylhexylsilyl. The reaction proceeds in the presence of a suitable catalyst (e.g. bis-triphenylphosphine palladium dichloride and copper(I) iodide as co-catalyst) in a suitable solvent (e.g. triethylamine). The intermediate F is treated with an acid anhydride such as, e.g. trifluoroacetic anhydride and the resulting trifluoroacetamide is cyclized to the 7-aza-indole intermediate G by treatment with a suitable catalyst (e.g. bis-triphenylphosphine palladium dichloride and copper (I) iodide as co-catalyst) in a suitable solvent such as, e.g. N,N-diisopropylethylamine. Removal of the silyl protective group with, e.g. tetra-n-butylammonium fluoride in a suitable solvent such as, e.g. tetrahydrofuran yields intermediate H which after oxidation of the alcohol with, e.g. manganese dioxide in, e.g. dichloromethane gives intermediate J. Boc-protection of the indole nitrogen using, e.g. di-tert-butyl dicarbonate in, e.g. dichloromethane yields intermediate K.

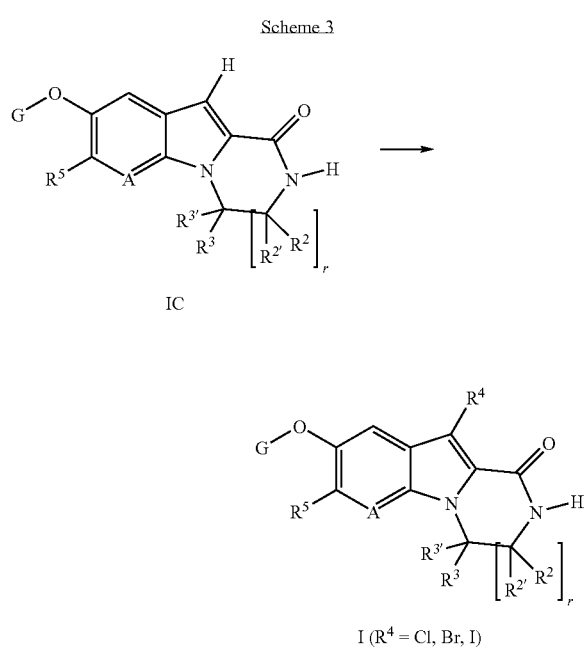

Scheme 3

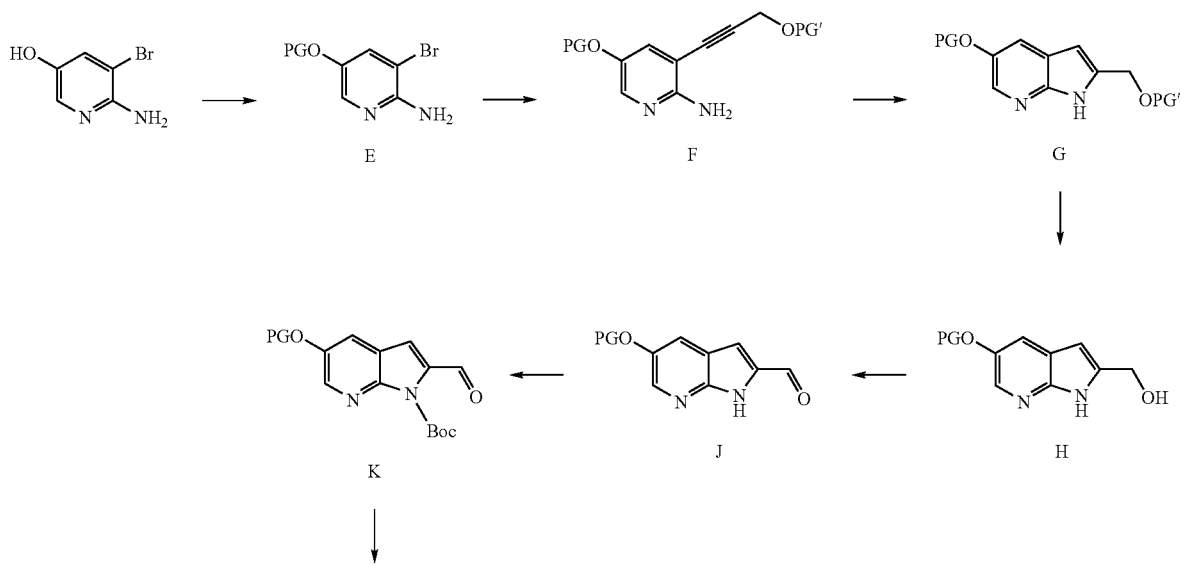

Scheme 4

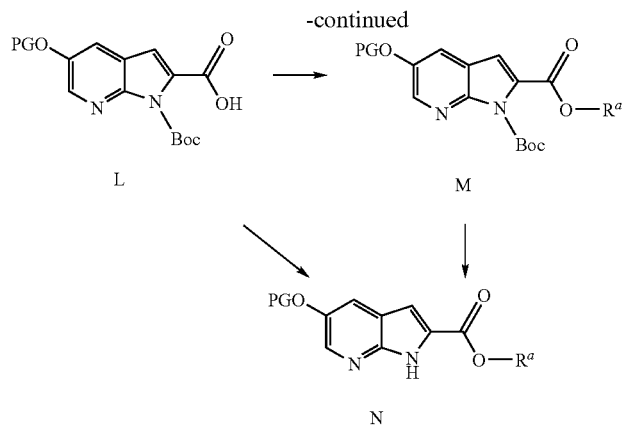

Oxidation of the aldehyde functionality according to methods known to those skilled in the art and described in literature (e.g. Amos B. Smith III et. al, J. Am. Chem. Soc. 1989, 111 (15), 5761-5768) yields intermediate L. Treatment of intermediate L with sulfuric acid in methanol furnishes intermediate N. In this case, $R^a$ signifies a methyl group. Intermediate N can also be obtained through removal of the Boc protective group from intermediate M under acidic conditions (e.g. with trifluoroacetic acid in, e.g. dichloromethane). Intermediate M in turn can be synthesized from intermediate L by treatment with a suitable base in a suitable solvent under anhydrous conditions (e.g. sodium hydride in N,N-dimethylformamide) and reaction of the intermediate anion with an alkylating agent $R^a$—X such as, e.g. methyl iodide. $R^a$ in scheme 4 is an alkyl group, preferably a lower alkyl group, preferably methyl or ethyl.

tions, such as e.g. meta-chloroperbenzoic acid in dichloromethane. The resulting intermediate O is then treated with a nucleophilic system, such as, e.g. ethyl chloroformate or benzoic acid bromide in the presence of a suitable base like, e.g. hexamethyldisilazane in a suitable solvent such as, e.g. tetrahydrofuran to furnish intermediate P. Intermediate P in turn can be further transformed via intermediates Q and R into aza-indole-2-carboxylates of formula S by methods outlined before. $R^a$ in scheme 5 is an alkyl group, preferably a lower alkyl group, preferably methyl or ethyl. PG signifies a protective group, such as, e.g. a benzyl protective group.

As described above, the compounds of formula I of the present invention can be used as medicaments for the treatment and/or prevention of diseases which are associated with the modulation of H3 receptors.

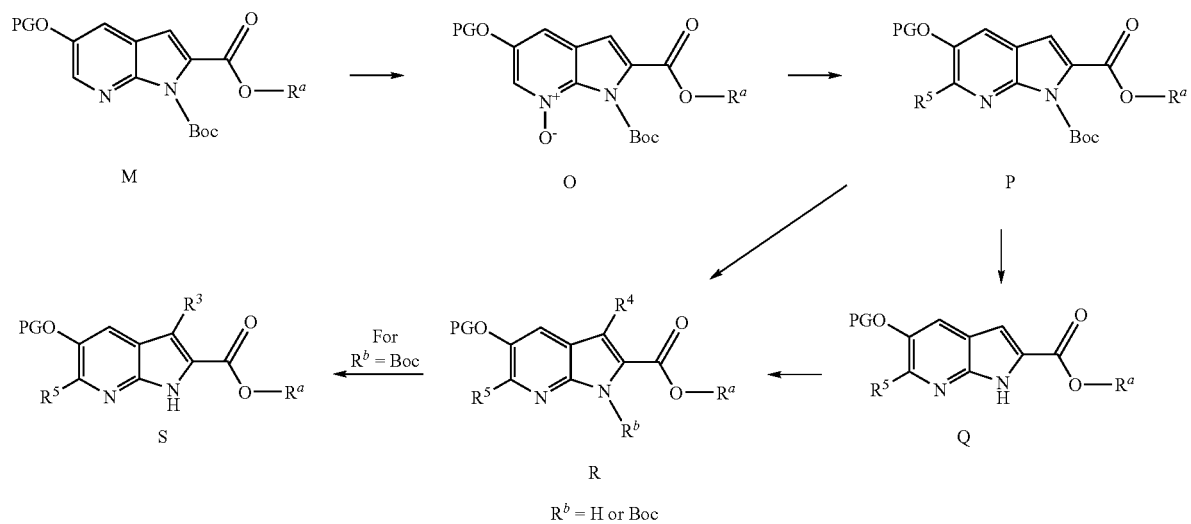

Aza-indole-2-carboxylates of formula S in which $R^5$ signifies a chlorine or bromine atom can be prepared from intermediates M (PG means a protective group such as, e.g. a benzyl protective group) which are oxidized at the pyridine nitrogen to the N-oxide under appropriate oxidizing condi- In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastrointestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, a minorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglinide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165, and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding assay with $^3$H—(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R)α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard topcounter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 μM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 μl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of [$^3$H]-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

| | $K_i$ (nM) |
|---|---|
| Example 5 | 6.5 |
| Example 78 | 17.1 |
| Example 92 | 28.8 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoA1 mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoA1 mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Example 1

8-(1-Isopropyl-piperidin-4-yloxy)-3,4-dihydro-2H-pyrazino[1,2-a]indol-1-one

To the suspension of 1.0 g (4.9 mmol) 8-hydroxy-3,4-dihydro-2H-pyrazino[1,2-a]indol-1-one in 70 ml tetrahydrofuran, a solution of 0.92 g (0.64 mmol) 1-isopropyl-piperidin-4-ol (commercially available) in 25 mL tetrahydrofuran, and 2.4 mL (2.0 g, 9.9 mmol) tributylphosphine were added. Another 20 mL tetrahydrofuran was added, and then the suspension was cooled to 0° C. Within 60 min., 2.5 g (9.9 mmol) 1,1'-(azodicarbonyl)dipiperidine was added under stirring and the reaction was allowed to reach room temperature. After 16 hours the suspension was filtered and the filtrate was evaporated. The residue was flash-chromatographed two times on silica gel with dichloromethane:methanol:ammonia (9:1:0.1 v/v) to give 0.43 g (26%) of the product as a light brown solid.

MS (ISP): 328.0 (M+H$^+$)

Intermediates

8-Hydroxy-3,4-dihydro-2H-pyrazino[1,2-a]indol-1-one

The solution of 10.1 g (21.8 mmol) 1-(2-tert-butoxycarbonylamino-ethyl)-5-(tert-butyl-dimethyl-silanyloxy)-1H-indole-2-carboxylic acid ethyl ester in 100 mL dichloromethane was cooled to 0° C. and 50.1 mL (74.7 g, 0.65 mol) trifluoroacetic acid were added dropwise within 5 min. The cooling bath was removed and after 1.5 hours the volatile components were removed at a rotary evaporator. The residue was dissolved in methanol and 12.1 g (87.5 mmol) potassium carbonate was added under cooling. The suspension was stirred for 64 hours at room temperature and then diluted with water. The solution was extracted three times with ethyl acetate and the combined organic layers were washed with brine, dried over magnesium sulfate, filtered and evaporated. The brown residue (5.3 g) was taken up in 20 mL tetrahydrofuran, the suspension was cooled to 0° C. and 21.8 mL (21.8 mmol; 1M solution in tetrahydrofuran) tetra-n-butylammonium fluoride solution was added. The cooling bath was removed and after 1 h stirring at room temperature the suspension was diluted with ethyl acetate and 10% aqueous ammonium chloride solution. Filtration gave a first batch of the product. The mother liquor was extracted six times with ethyl acetate. The combined organic layers were washed with water and brine, dried over magnesium sulfate, filtered and partially evaporated. The formed suspension was filtered and the filter cake was washed with ethyl acetate to give a second batch of compound, in total 1.9 g (43%) of a light brown solid.

MS (TIC): 203.2 (M+H$^+$)

1-(2-tert-Butoxycarbonylamino-ethyl)-5-(tert-butyl-dimethyl-silanyloxy)-1H-indole-2-carboxylic Acid Ethyl Ester The solution of 7.0 g (21.9 mmol) 5-(tert-butyl-dimethyl-silanyloxy)-1H-indole-2-carboxylic acid ethyl ester in 60 mL N,N-dimethylformamide was cooled down to 0° C. and 2.7 g (24.1 mmol) potassium tert-butoxide was added. After 30 min., 5.4 g (24.2 mmol) 2,2-dioxo-[1,2,3]oxathiazolidine-3-carboxylic acid tert-butyl ester (prepared according to WO 02/072584) was added and the cooling bath was removed. After 1.5 hours, 10% aqueous ammonium chloride solution was added and the two-phase mixture was extracted twice with ethyl acetate. The combined organic layers were washed with water and brine, dried over magnesium sulfate, filtered and evaporated. The thus obtained crude product (brown oil; 12.0 g, 100%) was used without further purification for the next step.

MS (EI): 463.3 (M)

5-(tert-Butyl-dimethyl-silanyloxy)-1H-indole-2-carboxylic Acid Ethyl Ester

To the solution of 10.0 g (49.0 mmol) 5-hydroxyindole-2-carboxylic acid (commercially available) in 30 ml N,N-dimethylformamide, 7.7 g (51.1 mmol) tert-butyldimethylchlorosilane and 3.5 g (51.4 mmol.) imidazole was added. After 1 hour, the solution was poured on 10% aqueous ammonium chloride solution and was extracted three times with ethyl acetate. The combined organic layers were washed with brine, dried over magnesium sulfate, filtered and evaporated. The residue was purified by column chromatography over silica gel with ethyl acetate:n-hexane (1:2 v/v) as eluant to give 15.3 g (98.5%) of the compound as a white solid.

MS (EI): 319.2 (M)

Example 2

8-(3-Piperidin-1-yl-propoxy)-3,4-dihydro-2H-pyrazino[1,2-a]indol-1-one

The suspension consistent of 0.27 g (0.97 mmol) 8-(3-chloro-propoxy)-3,4-dihydro-2H-pyrazino[1,2-a]indol-1-one, 0.16 g (1.2 mmol) potassium carbonate, 0.16 g (0.97 mmol) potassium iodide and 0.12 ml (99 µg, 1.2 mmol) piperidine (commercially available) in 10 mL 2-butanone was heated under reflux for 19 hours. After cooling down to room temperature the reaction mixture was poured on saturated aqueous sodium bicarbonate solution water and was extracted three times with dichloromethane. The combined organic layers were washed with brine, dried over magnesium sulfate, filtered and evaporated. The residue was flash-chromatographed on silica gel with dichloromethane: methanol: ammonia (9:1:0.1 v/v) as eluant to give 0.12 g (39%) of the desired compound as a colorless solid.

MS (TIC): 328.0 (M+H$^+$)

Intermediate 8-(3-Chloro-propoxy)-3,4-dihydro-2H-pyrazino[1,2-a]indol-1-one

The suspension consistent of 0.5 g (2.4 mmol) 8-hydroxy-3,4-dihydro-2H-pyrazino[1,2-a]indol-1-one (example 1, intermediate a), 0.41 g (2.6 mmol) potassium carbonate and 0.29 ml (0.47 g, 3.0 mmol) 1-bromo-3-chloropropane in 12 ml 2-butanone was heated under reflux for 64 hours. The reaction mixture was evaporated to dryness to give a light brown solid containing the desired product together with some starting material (0.58 g, 55%). This mixture was used in the next step without further purification.
MS (TIC): 279.3 (M+H$^+$) of product; 203.3 (M+H$^+$) starting material Example 3

8-(1-Cyclopropylmethyl-piperidin-4-yloxy)-3,4-dihydro-2H-pyrazino[1,2-a]indol-1-one To the solution of 0.27 g (0.95 mmol) 8-(piperidin-4-yloxy)-3,4-dihydro-2H-pyrazino[1,2-a]indol-1-one in 6 mL tetrahydrofuran, 20 μL water, 11 μL (99 μg, 1.42 mmol) cyclopropanecarboxaldehyde, 0.16 mL (0.17 g, 2.8 mmol) acetic acid and 1.42 mL (1.42 mmol, 1M solution in tetrahydrofuran) sodium cyanoborohydride were added and the reaction mixture was stirred for 18 hours at 55° C. The mixture was poured on 10% aqueous sodium bicarbonate and was extracted three times with ethyl acetate. The combined organic layers were washed with brine, dried over magnesium sulfate, filtered and evaporated. The residue was flash-chromatographed on silica gel with dichloromethane: methanol: ammonia (9:1:0.1 v/v) as eluant to give 96 μg (30%) of the desired compound as a white solid.
MS (TIC): 340.1 (M+H$^+$)

Intermediates 4-(1-Oxo-1,2,3,4-tetrahydro-pyrazino[1,2-a]indol-8-yloxy)-piperidine-1-carboxylic Acid Tert-Butyl Ester To the solution of 0.5 g (2.5 mmol) 8-hydroxy-3,4-dihydro-2H-pyrazino[1,2-a]indol-1-one (example 1, intermediate a)) in 10 mL tetrahydrofuran, 0.6 g (3.0 mmol) 1-(tert-butoxycarbonyl)-4-hydroxypiperidine and 0.78 g (3.0 mmol) triphenylphosphine were added. The solution was cooled to 0° C., 0.68 g (3.0 mmol) di-tert-butyl azodicarboxylate were added and the cooling bath was removed. After 18 hours the reaction mixture was evaporated and the residue was flash-chromatographed on silica gel with dichloromethane: methanol: ammonia (9:1:0.1 v/v) as eluant to give 0.46 g (49%) of the desired compound as a white solid.
MS (TIC): 386.2 (M+H$^+$)

8-(Piperidin-4-yloxy)-3,4-dihydro-2H-pyrazino[1,2-a]indol-1-one

The solution of 0.45 g (1.17 mmol) 4-(1-oxo-1,2,3,4-tetrahydro-pyrazino[1,2-a]indol-8-yloxy)-piperidine-1-carboxylic acid tert-butyl ester in 10 mL dichloromethane was cooled to 0° C. and was treated with 5 mL (7.4 g, 65.3 mmol) trifluoroacetic acid. The cooling bath was removed and after stirring at room temperature for 1 h the volatile components were removed at a rotary evaporator. The residue was taken up in dichloromethane and washed with 1 M aqueous sodium hydroxide solution. The organic phase was dried over magnesium sulfate, filtered and evaporated to give 140 mg (42%) of the product as a white solid.
MS (TIC): 286.0 (M+H$^+$)

Example 4

8-[3-((R)-3-Hydroxy-pyrrolidin-1-yl)-propoxy]-3,4-dihydro-2H-pyrazino[1,2-a]indol-1-one The title compound was synthesized in analogy to example 2, from 8-(3-chloro-propoxy)-3,4-dihydro-2H-pyrazino[1,2-a]indol-1-one (example 2, intermediate) and (R)-3-hydroxy-pyrrolidine (commercially available), to give the desired product as colorless solid (22%).
MS (TIC): 330.2 (M+H$^+$)

Example 5

8-[3-((R)-2-Methyl-pyrrolidin-1-yl)-propoxy]-3,4-dihydro-2H-pyrazino[1,2-a]indol-1-one The title compound was synthesized in analogy to example 2, from 8-(3-chloro-propoxy)-3,4-dihydro-2H-pyrazino[1,2-a]indol-1-one (example 2, intermediate) and (R)-2-methylpyrrolidine (commercially available) to give the desired product as a light red solid (16%).
MS (ISP): 328.5 (M+H$^+$)

Example 6

8-[3-((S)-2-Methyl-pyrrolidin-1-yl)-propoxy]-3,4-dihydro-2H-pyrazino[1,2-a]indol-1-one The title compound was synthesized in analogy to example 2, from 8-(3-chloro-propoxy)-3,4-dihydro-2H-pyrazino[1,2-a]indol-1-one (example 2, intermediate) and (S)-2-methylpyrrolidine (commercially available), to give the desired product as a white solid (10%).
MS (ISP): 328.3 (M+H$^+$)

Example 7

8-[3-((2S,5S)-2,5-Dimethyl-pyrrolidin-1-yl)-propoxy]-3,4-dihydro-2H-pyrazino[1,2-a]indol-1-one The title compound was synthesized in analogy to example 2, from 8-(3-chloro-propoxy)-3,4-dihydro-2H-pyrazino[1,2-a]indol-1-one (example 2, intermediate) and (2R,5R)-(−)-trans-2,5-dimethylpyrrolidine (commercially available), to give the desired product as a white solid (7%).
MS (TIC): 342.1 (M+H$^+$)

Example 8

(R)-8-(1-Isopropyl-piperidin-4-yloxy)-4-methyl-3,4-dihydro-2H-pyrazino[1,2-a]indol-1-one The title compound was synthesized in analogy to example 1, from (R)-8-hydroxy-4-methyl-3,4-dihydro-2H-pyrazino[1,2-a]indol-1-one, 1-isopropyl-piperidin-4-ol (commercially available), tributylphosphine and 1,1'-(azodicarbonyl) dipiperidine, to give the desired product as a colorless gum (22%).
MS (TIC): 342.0 (M+H$^+$)

Intermediates

(R)-8-Hydroxy-4-methyl-3,4-dihydro-2H-pyrazino[1,2-a]indol-1-one

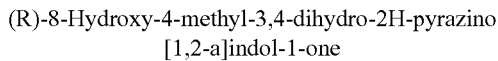

The solution of 0.60 g (1.26 mmol) 1-((R)-2-tert-butoxycarbonylamino-1-methyl-ethyl)-5-(tert-butyl-dimethyl-silanyloxy)-1H-indole-2-carboxylic acid ethyl ester in 8 mL dichloromethane was cooled to 0° C. and 1.9 mL (2.8 g, 24.9 mmol) trifluoroacetic acid was added dropwise within 5 min. The cooling bath was removed and after 1.5 hours the volatile components were removed at a rotary evaporator. The residue was dissolved in methanol, cooled to 0° C. and 0.69 g (5.0 mmol) potassium carbonate was added. The suspension was stirred for 6 hours at room temperature, diluted with water and ethyl acetate and the layers were separated. The aqueous phase was extracted twice with ethyl acetate. The combined organic layers were washed with brine, dried over magnesium sulfate, filtered and evaporated. The crude product was purified by flash column chromatography on silica gel with ethyl acetate as eluant to give 0.15 g (57%) of the desired product as a light brown gum.

MS (TIC): 217.0 (M+H$^+$)

1-((R)-2-tert-Butoxycarbonylamino-1-methyl-ethyl)-5-(tert-butyl-dimethyl-silanyloxy)-1H-indole-2-carboxylic Acid Ethyl Ester The title compound was synthesized in analogy to example 1, intermediate b), from 5-(tert-butyl-dimethyl-silanyloxy)-1H-indole-2-carboxylic acid ethyl ester (example 1, intermediate c)), (S)-5-methyl-2,2-dioxo-[1,2,3]oxathiazolidine-3-carboxylic acid tert-butyl ester (prepared according to WO02/010169) and potassium tert-butoxide, to give the desired compound as a brown oil (98%).

MS (TIC): 494.3 (M+NH$_4^+$); 477.1 (M+H$^+$)

Example 9

(R)-4-Methyl-8-(3-piperidin-1-yl-propoxy)-3,4-dihydro-2H-pyrazino[1,2-a]indol-1-one

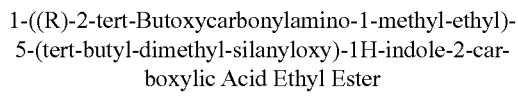

The title compound was synthesized in analogy to example 2, from (R)-8-(3-chloro-propoxy)-4-methyl-3,4-dihydro-2H-pyrazino[1,2-a]indol-1-one, piperidine (commercially available), potassium carbonate and potassium iodide, to give the desired product as a light yellow solid (71%).

MS (TIC): 342.0 (M+H$^+$)

Intermediate

(R)-8-(3-Chloro-propoxy)-4-methyl-3,4-dihydro-2H-pyrazino[1,2-a]indol-1-one The title compound was synthesized in analogy to example 2, intermediate, from (R)-8-hydroxy-4-methyl-3,4-dihydro-2H-pyrazino[1,2-a]indol-1-one, potassium carbonate and 1-bromo-3-chloropropane, to give the title compound as a light yellow solid (56%).

MS (TIC): 293.0 (M+H$^+$)

Example 10

(R)-8-[3-((R)-3-Hydroxy-pyrrolidin-1-yl)-propoxy]-4-methyl-3,4-dihydro-2H-pyrazino[1,2-a]indol-1-one

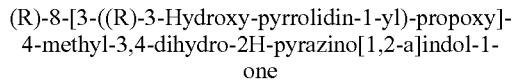

The title compound was synthesized in analogy to example 2 from (R)-8-(3-chloro-propoxy)-4-methyl-3,4-dihydro-2H-pyrazino[1,2-a]indol-1-one (example 9, intermediate), (R)-3-hydroxy-pyrrolidine (commercially available), potassium carbonate and potassium iodide, to give the desired product as a light brown foam (39%).

MS (TIC): 344.1 (M+H$^+$)

Example 11

(S)-8-(1-Isopropyl-piperidin-4-yloxy)-4-methyl-3,4-dihydro-2H-pyrazino[1,2-a]indol-1-one

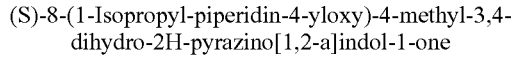

The title compound was synthesized in analogy to example 1, from (S)-8-hydroxy-4-methyl-3,4-dihydro-2H-pyrazino[1,2-a]indol-1-one, 1-isopropyl-piperidin-4-ol (commercially available), triphenylphosphine and di-tert-butyl-azodicarboxylate, to give the desired product as a light yellow foam (52%).

MS (TIC): 342.1 (M+H$^+$)

Intermediates

(S)-8-Hydroxy-4-methyl-3,4-dihydro-2H-pyrazino[1,2-a]indol-1-one

The suspension consistent of 3.50 g (11.4 mmol) (S)-8-benzyloxy-4-methyl-3,4-dihydro-2H-pyrazino[1,2-a]indol-1-one and 0.35 g palladium on activated charcoal (10% Pd; commercially available) in 40 mL methanol was hydrogenated at room temperature at 1.5 bar for 3 hours. The reaction mixture was filtered over Dicalite Speed Plus® (Aldrich) and the volatile components were evaporated at a rotary evaporator to give the desired compound as a light yellow foam (100%) which was used in the next step without further purification.

MS (TIC): 217.1 (M+H$^+$)

(S)-8-Benzyloxy-4-methyl-3,4-dihydro-2H-pyrazino[1,2-a]indol-1-one

The title compound was synthesized in analogy to example 8, intermediate a), from 5-benzyloxy-1-((S)-2-tert-butoxycarbonylamino-1-methyl-ethyl)-1H-indole-2-carboxylic acid ethyl ester, to give the title compound as a light yellow solid (69%).

MS (TIC): 307.1 (M)

5-Benzyloxy-1-((S)-2-tert-butoxycarbonylamino-1-methyl-ethyl)-1H-indole-2-carboxylic Acid Ethyl Ester The title compound was synthesized in analogy to example 8, intermediate a), from ethyl 5-benzyloxyindole-2-carboxylate (commercially available), (R)-5-methyl-2,2-dioxo-[1,2,3]oxathiazolidine-3-carboxylic acid tert-butyl ester (prepared according to WO02/010169) and potassium tert-butoxide, to give the desired compound as a yellow solid (100%).

MS (EI): 452.2 (M)

Example 12

(S)-4-Hydroxymethyl-8-(1-isopropyl-piperidin-4-yloxy)-3,4-dihydro-2H-pyrazino[1,2-a]indol-1-one The solution of 0.2 g (0.40 mmol) (S)-4-[dimethyl-(1,1,2-trimethyl-propyl)-silanyloxymethyl]-8-(1-isopropyl-piperidin-4-yloxy)-3,4-dihydro-2H-pyrazino[1,2-a]indol-1-one in 1 ml tetrahydrofuran was cooled down to 0° C. and treated with 0.14 ml (0.126 g, 0.48 mmol) tetra-n-butylammonium-fluoride solution (1M in tetrahydrofuran). The cooling bath was removed and after 1.5 hours stirring at room temperature the solution was poured on saturated aqueous sodium bicarbonate solution and was extracted three times with ethyl acetate. The combined organic layers were washed with brine, dried over magnesium sulfate, filtered and evaporated. The crude product was purified by flash column chromatography on silica gel with dichloromethane:methanol:ammonia (9:1:0.1 v/v) as eluant to give 60 µg (42%) of the desired compound as a colorless semi solid.

MS (ISP): 358.1 (M+H$^+$)

Intermediates (S)-4-[Dimethyl-(1,1,2-trimethyl-propyl)-silanyloxymethyl]-8-(1-isopropyl-piperidin-4-yloxy)-3,4-dihydro-2H-pyrazino[1,2-a]indol-1-one The title compound was synthesized in analogy to example 1, from (S)-4-[dimethyl-(1,1,2-trimethyl-propyl)-silanyloxymethyl]-8-hydroxy-3,4-dihydro-2H-pyrazino[1,2-a]indol-1-one, 1-isopropyl-piperidin-4-ol (commercially available), triphenylphosphine and di-tert-butyl-azodicarboxylate, to give the desired product as a light yellow foam (40%).

MS (TIC): 500.2 (M+H$^+$)

(S)-4-[Dimethyl-(1,1,2-trimethyl-propyl)-silanyloxymethyl]-8-hydroxy-3,4-dihydro-2H-pyrazino[1,2-a]indol-1-one The title compound was synthesized in analogy to example 11, intermediate a), through hydrogenation of (S)-8-benzyloxy-4-[dimethyl-(1,1,2-trimethyl-propyl)-silanyloxymethyl]-3,4-dihydro-2H-pyrazino[1,2-a]indol-1-one, to give the desired product as a colorless foam (100%).

MS (TIC): 375.3 (M+H$^+$)

(S)-8-Benzyloxy-4-[dimethyl-(1,1,2-trimethyl-propyl)-silanyloxymethyl]-3,4-dihydro-2H-pyrazino[1,2-a]indol-1-one The title compound was synthesized in analogy to example 8, intermediate a), from 5-benzyloxy-1-{(S)-1-(tert-butoxycarbonylamino-methyl)-2-[dimethyl-(1,1,2-trimethyl-propyl)-silanyloxy]-ethyl}-1H-indole-2-carboxylic acid ethyl ester to give a mixture of the desired compound and the unprotected hydroxymethyl compound. The mixture was dissolved in N,N-dimethylformamide and 1 equivalent of imidazole was added. At 0° C., 1 equivalent of dimethylhexylsilyl chloride was added and the cooling bath was removed. The reaction mixture was poured on water and was extracted twice with ethyl acetate. The combined organic layers were washed with brine, dried over magnesium sulfate, filtered and evaporated. The residue was purified by column chromatography over silica gel using n-hexane:ethyl acetate (1:2 v/v) as eluant to give the desired product as a light yellow foam (35%).

MS (TIC): 465.2 (M+H$^+$)

5-Benzyloxy-1-{(S)-1-(tert-butoxycarbonylamino-methyl)-2-[dimethyl-(1,1,2-trimethyl-propyl)-silanyloxy]-ethyl}-1H-indole-2-carboxylic Acid Ethyl Ester The title compound was synthesized in analogy to example 8, intermediate a), from ethyl 5-benzyloxyindole-2-carboxylate (commercially available), (R)-5-[dimethyl(1,1,2-trimethylpropyl)silanyloxymethyl]-2,2-dioxo-[1,2,3]oxathiazolidine-3-carboxylic acid tert-butyl ester (prepared according to WO02/010169) and potassium tert-butoxide, to give the desired compound as a light yellow oil (>100%). The so-obtained product was used in the next step without further purification.

MS (EI): 610.4 (M); 469.2 (M-(C$_4$H$_8$+CO$_2$+C$_3$H$_7$))

Example 13

(S)-8-(1-Isopropyl-piperidin-4-yloxy)-3-methyl-3,4-dihydro-2H-pyrazino[1,2-a]indol-1-one The title compound was synthesized in analogy to example 1, from (S)-8-hydroxy-3-methyl-3,4-dihydro-2H-pyrazino[1,2-a]indol-1-one, 1-isopropyl-piperidin-4-ol (commercially available), triphenylphosphine and di-tert-butyl-azodicarboxylate, to give the desired product as a light yellow solid (46%).

MS (TIC): 342.0 (M+H$^+$)

Intermediates (S)-8-Hydroxy-3-methyl-3,4-dihydro-2H-pyrazino[1,2-a]indol-1-one The title compound was synthesized in analogy to example 11, intermediate a), through hydrogenation of (S)-8-benzyloxy-3-methyl-3,4-dihydro-2H-pyrazino[1,2-a]indol-1-one, to give the product as a light yellow solid (93%).

MS (EI): 216.1 (M)

(S)-8-Benzyloxy-3-methyl-3,4-dihydro-2H-pyrazino[1,2-a]indol-1-one

The title compound was synthesized in analogy to example 8, intermediate a), from 5-benzyloxy-1-((S)-2-tert-butoxycarbonylamino-propyl)-1H-indole-2-carboxylic acid ethyl ester, to give the desired compound as a light yellow solid (68%).

MS (TIC): 307.4 (M+H$^+$)

5-Benzyloxy-1-((S)-2-tert-butoxycarbonylamino-propyl)-1H-indole-2-carboxylic Acid Ethyl Ester The title compound was synthesized in analogy to example 1, intermediate b), from ethyl 5-benzyloxyindole-2-carboxylate (commercially available), (S)-4-methyl-2,2-dioxo-[1,2,3]oxathiazolidine-3-carboxylic acid tert-butyl ester (prepared according to WO02/010169) and potassium tert-butoxide, to give the desired compound as a light yellow solid (>100%). The so-obtained product was used in the next step without further purification.

MS (TIC): 452.2 (M)

Example 14

(R)-8-(1-Isopropyl-piperidin-4-yloxy)-3-methyl-3,4-dihydro-2H-pyrazino[1,2-a]indol-1-one The title compound was synthesized in analogy to example 1, from (R)-8-hydroxy-3-methyl-3,4-dihydro-2H-pyrazino[1,2-a]indol-1-one, 1-isopropyl-piperidin-4-ol (commercially available), triphenylphosphine and di-tert-butyl-azodicarboxylate, to give the desired product as a light yellow solid (34%).

MS (TIC): 342.0 (M+H$^+$)

Intermediates

(R)-8-Hydroxy-3-methyl-3,4-dihydro-2H-pyrazino[1,2-a]indol-1-one

The title compound was synthesized in analogy to example 11, intermediate a), through hydrogenation of (R)-8-benzyloxy-3-methyl-3,4-dihydro-2H-pyrazino[1,2-a]indol-1-one, to give the product as a light yellow solid (>100%). The so-obtained product was used in the next step without further purification.

MS (ISP): 217.2 (M+H$^+$)

(R)-8-Benzyloxy-3-methyl-3,4-dihydro-2H-pyrazino[1,2-a]indol-1-one

The title compound was synthesized in analogy to example 8, intermediate a), from 5-benzyloxy-1-((R)-2-tert-butoxycarbonylamino-propyl)-1H-indole-2-carboxylic acid ethyl ester, to give the desired compound as a light yellow solid (68%).

MS (TIC): 307.4 (M+H$^+$)

5-Benzyloxy-1-((R)-2-tert-butoxycarbonylamino-propyl)-1H-indole-2-carboxylic Acid Ethyl Ester The title compound was synthesized in analogy to example 1, intermediate b), from ethyl 5-benzyloxyindole-2-carboxylate (commercially available), (R)-4-methyl-2,2-dioxo-[1,2,3]oxathiazolidine-3-carboxylic acid tert-butyl ester (prepared according to WO02/010169) and potassium tert-butoxide, to give the desired compound as a light yellow solid (>100%). The so-obtained product was used in the next step without further purification.

MS (TIC): 452.2 (M)

Example 15

9-(1-Isopropyl-piperidin-4-yloxy)-2,3,4,5-tetrahydro-[1,4]diazepino[1,2-a]indol-1-one The title compound was synthesized in analogy to example 1, from 9-hydroxy-2,3,4,5-tetrahydro-[1,4]diazepino[1,2-a]indol-1-one, 1-isopropyl-piperidin-4-ol (commercially available), triphenylphosphine and di-tert-butyl-azodicarboxylate, to give the desired product as a light yellow oil (13%).

MS (TIC): 342.4 (M+H$^+$)

Intermediates

9-Hydroxy-2,3,4,5-tetrahydro-[1,4]diazepino[1,2-a]indol-1-one

The title compound was synthesized in analogy to example 11, intermediate a), through hydrogenation of 9-benzyloxy-2,3,4,5-tetrahydro-[1,4]diazepino[1,2-a]indol-1-one, to give the product as a light yellow solid (45%).

MS (EI): 217.1 (M+H$^+$)

9-Benzyloxy-2,3,4,5-tetrahydro-[1,4]diazepino[1,2-a]indol-1-one

To the solution of 0.6 g (1.70 mmol) 1-(3-amino-propyl)-5-benzyloxy-1H-indole-2-carboxylic acid ethyl ester in 6 mL N,N-dimethylformamide, 85 µg (1.95 mmol; 55% dispersion in mineral oil) sodium hydride was added. After 2 hours the reaction mixture was diluted with water and dichloromethane, the phases were separated and the aqueous phase was washed three times with dichloromethane. The combined organic layers were washed with brine, dried over magnesium sulfate, filtered and evaporated. The crude product was purified by flash column chromatography on silica gel with dichloromethane: methanol:ammonia (9:1:0.1 v/v) to give the desired compound as a light yellow solid (67%).

MS (TIC): 307.1 (M+H$^+$)

1-(3-Amino-propyl)-5-benzyloxy-1H-indole-2-carboxylic Acid Ethyl Ester

The solution of 14.3 g (31.6 mmol) 5-benzyloxy-1-(3-tert-butoxycarbonylamino-propyl)-1H-indole-2-carboxylic acid ethyl ester in 140 mL dichloromethane was cooled to 0° C. and 70 mL (104.2 g, 914 mmol) trifluoroacetic acid was added. The cooling bath was removed and after stirring at room temperature for 1 h, the solution was neutralized with 1M aqueous sodium hydroxide solution and was extracted with dichloromethane. The organic phase was washed with brine, dried over magnesium sulfate, filtered and evaporated to give the crude product as yellow oil (>100%). The compound was pure enough for the next step without further purification.

MS (TIC): 353.2 (M+H$^+$)

5-Benzyloxy-1-(3-tert-butoxycarbonylamino-propyl)-1H-indole-2-carboxylic Acid Ethyl Ester The title compound was synthesized in analogy to example 1, intermediate b), from ethyl 5-benzyloxyindole-2-carboxylate (commercially available), 2,2-dioxo-2$\lambda'$-[1,2,3]oxathiazinane-3-carboxylic acid tert-butyl ester (prepared according to WO03/037327) and potassium tert-butoxide, to give the desired compound as a light yellow oil (99%). The so-obtained product was used in the next step without further purification.

MS (TIC): 453.3 (M+H$^+$); 353.2 (M-($C_4H_8$+$CO_2$))

Example 16

9-(3-Pyrrolidin-1-yl-propoxy)-2,3,4,5-tetrahydro-[1,4]diazepino[1,2-a]indol-1-one The title compound was synthesized in analogy to example 2, from 9-(3-chloro-propoxy)-2,3,4,5-tetrahydro-[1,4]diazepino[1,2-a]indol-1-one, pyrrolidine (commercially available) and potassium carbonate, to give the desired product as a light yellow solid (50%).
MS (TIC): 328.1 (M+H$^+$)

Intermediate

9-(3-Chloro-propoxy)-2,3,4,5-tetrahydro-[1,4]diazepino[1,2-a]indol-1-one

The title compound was synthesized in analogy to example 2, intermediate, from 9-hydroxy-2,3,4,5-tetrahydro-[1,4]diazepino[1,2-a]indol-1-one (example 15, intermediate a)), potassium carbonate and 1-bromo-3-chloropropane, to give the desired compound as a light yellow solid (35%).
MS (TIC): 293.0 (M+H$^+$)

Example 17

2-Cyclopropylmethyl-8-(1-isopropyl-piperidin-4-yloxy)-3,4-dihydro-2H-pyrazino[1,2-a]indol-1-one To the solution of 0.15 g (0.46 mmol) 8-(1-isopropyl-piperidin-4-yloxy)-3,4-dihydro-2H-pyrazino[1,2-a]indol-1-one (example 1) in 3 mL N,N-dimethylformamide, 24 mg (0.55 mmol, 55% dispersion in mineral oil) sodium hydride was added. After 30 min., 1-(bromomethyl)cyclopropane was added and the mixture was stirred until completion of the reaction as indicated by TLC (2 h). The reaction mixture was poured on 10% aqueous ammonium chloride solution and was extracted three times with ethyl acetate. The organic layers were washed with water and brine, dried over magnesium sulfate, filtered and evaporated. The residue was purified by flash column chromatography on silica gel with dichloromethane:methanol:ammonia (9:1:0.1 v/v) to give the desired compound as a white solid (38%).
MS (TIC): 382.4 (M+H$^+$)

Example 18

8-(1-Isopropyl-piperidin-4-yloxy)-2-(2-methoxyethyl)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 2-bromoethyl methyl ether, to give the product as a white solid (28%).
MS (TIC): 386.3 (M+H$^+$)

Example 19

8-(1-Isopropyl-piperidin-4-yloxy)-2-(2,2,2-trifluoroethyl)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 2,2,2-trifluoroethyl trifluoromethanesulfonate, to give the title compound as a white solid (19%).
MS (TIC): 410.3 (M+H$^+$)

Example 20

8-(1-Isopropyl-piperidin-4-yloxy)-2-methyl-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and methyl iodide, to give the desired product as a colorless solid (22%).
MS (TIC): 342.0 (M+H$^+$)

Example 21

2-Ethyl-8-(1-isopropyl-piperidin-4-yloxy)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and ethyl bromide, to give the desired product as white solid (78%).
MS (TIC): 356.2 (M+H$^+$)

Example 22

2-Isopropyl-8-(1-isopropyl-piperidin-4-yloxy)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 2-bromopropane, to give the desired product as white solid (10%).
MS (TIC): 370.2 (M+H$^+$)

Example 23

(R)-2-Cyclopropylmethyl-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and 1-(bromomethyl)cyclopropane, to give the desired product as a light yellow oil (47%).
MS (TIC): 396.1 (M+H$^+$)

Example 24

(R)-8-(1-Isopropyl-piperidin-4-yloxy)-2-(2-methoxy-ethyl)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), 2-bromoethyl methyl ether and sodium hydride, to give the desired product as a light yellow oil (26%).
MS (TIC): 400.3 (M+H$^+$)

Example 25

(R)-8-(1-Isopropyl-piperidin-4-yloxy)-2,4-dimethyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), methyl iodide and sodium hydride, to give the desired product as a light yellow oil (19%).

MS (TIC): 356.2 (M+H$^+$)

Example 26

(R)-8-(1-Isopropyl-piperidin-4-yloxy)-4-methyl-2-(2,2,2-trifluoro-ethyl)-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), 2,2,2-trifluoroethyl trifluoromethanesulfonate and sodium hydride, to give the desired product as a colorless oil (28%).

MS (TIC): 424.2 (M+H$^+$)

Example 27

(R)-2-Ethyl-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), ethyl bromide and sodium hydride, to give the desired product as a colorless oil (76%).

MS (TIC): 370.2 (M+H$^+$)

Example 28

(S)-2-Cyclopropylmethyl-8-(1-isopropyl-piperidin-4-yloxy)-4-methyl-3,4-dihydro-2H-pyrazino[1,2-a]indol-1-one The title compound was synthesized in analogy to example 17, from (S)-8-(1-isopropyl-piperidin-4-yloxy)-4-methyl-3,4-dihydro-2H-pyrazino[1,2-a]indol-1-one (example 11), sodium hydride and 1-(bromomethyl)cyclopropane, to give the desired product as a light yellow solid (55%).

MS (TIC): 396.1 (M+H$^+$)

Example 29

(S)-8-(1-Isopropyl-piperidin-4-yloxy)-2-(2-methoxy-ethyl)-4-methyl-3,4-dihydro-2H-pyrazino[1,2-a]indol-1-one The title compound was synthesized in analogy to example 17, from (S)-8-(1-isopropyl-piperidin-4-yloxy)-4-methyl-3,4-dihydro-2H-pyrazino[1,2-a]indol-1-one (example 11), 2-bromoethyl methyl ether and sodium hydride, to give the desired product as a colorless oil (50%).

MS (TIC): 400.3 (M+H$^+$)

Example 30

(S)-2-Cyclopropylmethyl-8-(1-isopropyl-piperidin-4-yloxy)-3-methyl-3,4-dihydro-2H-pyrazino[1,2-a]indol-1-one The title compound was synthesized in analogy to example 17, from (S)-8-(1-isopropyl-piperidin-4-yloxy)-3-methyl-3,4-dihydro-2H-pyrazino[1,2-a]indol-1-one (example 13), 1-(bromomethyl)cyclopropane and sodium hydride, to give the desired product as a colorless oil (47%).

MS (TIC): 396.1 (M+H$^+$)

Example 31

(S)-8-(1-Isopropyl-piperidin-4-yloxy)-2-(2-methoxy-ethyl)-3-methyl-3,4-dihydro-2H-pyrazino[1,2-a]indol-1-one The title compound was synthesized in analogy to example 17, from (S)-8-(1-isopropyl-piperidin-4-yloxy)-3-methyl-3,4-dihydro-2H-pyrazino[1,2-a]indol-1-one (example 13), 2-bromoethyl methyl ether and sodium hydride, to give the desired product as a colorless oil (30%).

MS (TIC): 400.3 (M+H$^+$)

Example 32

(R)-2-Cyclopropylmethyl-8-(1-isopropyl-piperidin-4-yloxy)-3-methyl-3,4-dihydro-2H-pyrazino[1,2-a]indol-1-one The title compound was synthesized in analogy to example 17, from (R)-8-(1-isopropyl-piperidin-4-yloxy)-3-methyl-3,4-dihydro-2H-pyrazino[1,2-a]indol-1-one (example 14), 1-(bromomethyl)cyclopropane and sodium hydride, to give the compound as a colorless oil (77%).

MS (TIC): 396.1 (M+H$^+$)

Example 33

(R)-8-(1-Isopropyl-piperidin-4-yloxy)-2-(2-methoxy-ethyl)-3-methyl-3,4-dihydro-2H-pyrazino[1,2-a]indol-1-one The title compound was synthesized in analogy to example 17, from (R)-8-(1-isopropyl-piperidin-4-yloxy)-3-methyl-3,4-dihydro-2H-pyrazino[1,2-a]indol-1-one (example 14), 2-bromoethyl methyl ether and sodium hydride, to give the desired product as a colorless oil (49%).

MS (TIC): 400.3 (M+H$^+$)

Example 34

2-[8-(1-Isopropyl-piperidin-4-yloxy)-1-oxo-3,4-dihydro-1H-pyrazino[1,2-a]indol-2-yl]-acetamide The title compound was synthesized in analogy to example 17, from 8-(1-isopropyl-piperidin-4-yloxy)-3,4-dihydro-2H-pyrazino[1,2-a]indol-1-one (example 1), sodium hydride and 2-bromoacetamide, to give the desired product as a white solid (6%).

MS (TIC): 385.1 (M+H$^+$)

Example 35

2-[8-(1-Isopropyl-piperidin-4-yloxy)-1-oxo-3,4-dihydro-1H-pyrazino[1,2-a]indol-2-yl]-N-methyl-acetamide The title compound was synthesized in analogy to example 17, from 8-(1-isopropyl-piperidin-4-yloxy)-3,4-dihydro-2H-pyrazino[1,2-a]indol-1-one (example 1), sodium hydride and 2-chloro-N-methylacetamide, to give the desired product in a yield of 68%.

MS (TIC): 399.3 (M+H$^+$)

Example 36

2-[8-(1-Isopropyl-piperidin-4-yloxy)-1-oxo-3,4-dihydro-1H-pyrazino[1,2-a]indol-2-yl]-N,N-dimethyl-acetamide The title compound was synthesized in analogy to example 17, from 8-(1-isopropyl-piperidin-4-yloxy)-3,4-dihydro-2H-pyrazino[1,2-a]indol-1-one (example 1), sodium hydride and 2-chloro-N,N-dimethylacetamide, to give the desired product as a white solid (71%).

MS (TIC): 414.3 (M+H$^+$)

Example 37

8-(1-Isopropyl-piperidin-4-yloxy)-2-(2-morpholin-4-yl-2-oxo-ethyl)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 4-(2-chloroacetyl)morpholine, to give the desired product as a white foam (10%).

MS (TIC): 455.4 (M+H$^+$)

Example 38

N-Isopropyl-2-[8-(1-isopropyl-piperidin-4-yloxy)-1-oxo-3,4-dihydro-1H-pyrazino[1,2-a]indol-2-yl]-acetamide The title compound was synthesized in analogy to example 17, from 8-(1-isopropyl-piperidin-4-yloxy)-3,4-dihydro-2H-pyrazino[1,2-a]indol-1-one (example 1), N-isopropyl chloroacetamide and sodium hydride, to give the desired product as a white solid (79%).

MS (TIC): 427.3 (M+H$^+$)

Example 39

N,N-Diisopropyl-2-[8-(1-isopropyl-piperidin-4-yloxy)-1-oxo-3,4-dihydro-1H-pyrazino[1,2-a]indol-2-yl]-acetamide The title compound was synthesized in analogy to example 17, from 8-(1-isopropyl-piperidin-4-yloxy)-3,4-dihydro-2H-pyrazino[1,2-a]indol-1-one (example 1), 2-chloro-N,N-diisopropyl-acetamide and sodium hydride, to give the desired product as a white solid (31%).

MS (TIC): 469.3 (M+H$^+$)

Example 40

2-[8-(1-Isopropyl-piperidin-4-yloxy)-1-oxo-3,4-dihydro-1H-pyrazino[1,2-a]indol-2-yl]-N-phenyl-acetamide The title compound was synthesized in analogy to example 17, from 8-(1-isopropyl-piperidin-4-yloxy)-3,4-dihydro-2H-pyrazino[1,2-a]indol-1-one (example 1), sodium hydride and 2-chloro-N-phenylacetamide, to give the desired product as a white solid (14%).

MS (TIC): 461.2 (M+H$^+$)

Example 41

2-Benzyl-8-(1-isopropyl-piperidin-4-yloxy)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and benzyl bromide, to give the desired product as a white solid (66%).

MS (TIC): 418.1 (M+H$^+$)

Example 42

8-(1-Isopropyl-piperidin-4-yloxy)-2-(2-trifluoromethyl-benzyl)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 2-(trifluoromethyl)benzyl bromide, to give the desired product as a light yellow foam (93%).

MS (TIC): 486.2 (M+H$^+$)

Example 43

8-(1-Isopropyl-piperidin-4-yloxy)-2-(3-trifluoromethyl-benzyl)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 3-(trifluoromethyl)benzyl bromide, to give the desired product as a white solid (74%).

MS (TIC): 486.3 (M+H$^+$)

Example 44

8-(1-Isopropyl-piperidin-4-yloxy)-2-(4-trifluoromethyl-benzyl)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 4-(trifluoromethyl)benzyl bromide, to give the desired product as a white solid (74%).

MS (TIC): 486.2 (M+H$^+$)

Example 45

8-(1-Isopropyl-piperidin-4-yloxy)-2-(2-methoxybenzyl)-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride and 2-methoxybenzyl chloride, to give the desired product as a white solid (54%).

MS (TIC): 448.2 (M+H$^+$)

Example 46

8-(1-Isopropyl-piperidin-4-yloxy)-2-(3-methoxybenzyl)-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride and 3-methoxybenzyl chloride, to give the desired product as a white solid (74%).

MS (TIC): 448.2 (M+H$^+$)

Example 47

8-(1-Isopropyl-piperidin-4-yloxy)-2-(4-methoxybenzyl)-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride and 4-methoxybenzyl chloride, to give the desired product as a white solid (50%).

MS (TIC): 448.2 (M+H$^+$)

Example 48

2-(2-Fluoro-benzyl)-8-(1-isopropyl-piperidin-4-yloxy)-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride and 2-fluorobenzyl chloride, to give the desired product as a white solid (77%).

MS (TIC): 436.2 (M+H$^+$)

Example 49

2-(3-Fluoro-benzyl)-8-(1-isopropyl-piperidin-4-yloxy)-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride and 3-fluorobenzyl bromide, to give the desired product as a white solid (79%).

MS (TIC): 436.2 (M+H$^+$)

Example 50

2-(4-Fluoro-benzyl)-8-(1-isopropyl-piperidin-4-yloxy)-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride and 4-fluorobenzyl bromide, to give the desired product as a white solid (69%).

MS (TIC): 436.2 (M+H$^+$)

Example 51

2-[8-(1-Isopropyl-piperidin-4-yloxy)-1-oxo-3,4-dihydro-1H-pyrazino[1,2-a]indol-2-ylmethyl]-benzonitrile

The title compound was synthesized in analogy to example 17, from 8-(1-isopropyl-piperidin-4-yloxy)-3,4-dihydro-2H-pyrazino[1,2-a]indol-1-one (example 1), sodium hydride and 2-cyanobenzyl bromide, to give the desired product as a light yellow solid (81%).

MS (TIC): 443.2 (M+H$^+$)

Example 52

3-[8-(1-Isopropyl-piperidin-4-yloxy)-1-oxo-3,4-dihydro-1H-pyrazino[1,2-a]indol-2-ylmethyl]-benzonitrile

The title compound was synthesized in analogy to example 17, from 8-(1-isopropyl-piperidin-4-yloxy)-3,4-dihydro-2H-pyrazino[1,2-a]indol-1-one (example 1), sodium hydride and 3-cyanobenzyl bromide, to give the desired product as a white foam (66%).

MS (TIC): 443.2 (M+H$^+$)

Example 53

2-(2-Fluoro-benzyl)-8-(1-isopropyl-piperidin-4-yloxy)-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride and 4-cyanobenzyl bromide, to give the desired product as a white solid (73%).

MS (TIC): 443.2 (M+H$^+$)

Example 54

(R)-8-(1-Isopropyl-piperidin-4-yloxy)-4-methyl-2-pyridin-2-ylmethyl-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride (2.4 equivalents) and 2-(chloromethyl)pyridine hydrochloride, to give the desired product as a white solid (88%).

MS (TIC): 419.2 (M+H$^+$)

Example 55

8-(1-Isopropyl-piperidin-4-yloxy)-2-pyridin-3-ylmethyl-3,4-dihydro-2H-pyrazino[1,2-a]indol-1-one

The title compound was synthesized in analogy to example 17, from 8-(1-isopropyl-piperidin-4-yloxy)-3,4-dihydro-2H-pyrazino[1,2-a]indol-1-one (example 1), sodium hydride (2.4 equivalents) and 3-(chloromethyl)pyridine hydrochloride, to give the desired product as a white solid (78%).

MS (TIC): 419.2 (M+H$^+$)

Example 56

8-(1-Isopropyl-piperidin-4-yloxy)-2-pyridin-4-ylmethyl-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride (2.4 equivalents) and 4-(chloromethyl)pyridine hydrochloride, to give the desired product as a light yellow solid (74%).
MS (TIC): 419.2 (M+H$^+$)

Example 57

(RS)-8-(1-Isopropyl-piperidin-4-yloxy)-2-(1-phenyl-ethyl)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and (1-bromoethyl)benzene, to give the desired product as a white foam (67%).
MS (TIC): 432.3 (M+H$^+$)

Example 58

2-(3-Hydroxy-propyl)-8-(1-isopropyl-piperidin-4-yloxy)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and 3-bromo-1-propanol, to give the desired product as a white solid (66%).
MS (TIC): 386.2 (M+H$^+$)

Example 59

2-(2-Hydroxy-ethyl)-8-(1-isopropyl-piperidin-4-yloxy)-3,4-dihydro-2H-pyrazino[1,2-a]indol-1-one To a cooled solution of 0.145 g (0.30 mmol) 2-[2-(tert-butyl-dimethyl-silanyloxy)-ethyl]-8-(1-isopropyl-piperidin-4-yloxy)-3,4-dihydro-2H-pyrazino[1,2-a]indol-1-one in 3 mL dichloromethane, 1 mL (1.49 g, 13 mmol) trifluoroacetic acid was added and the cooling bath was removed. The solution was evaporated and the residue was taken up in ethyl acetate and was washed with 1M aqueous sodium hydroxide solution and brine. The organic layer was dried over magnesium sulfate, filtered and evaporated. The residue was purified by flash column chromatography on silica gel with dichloromethane: methanol:ammonia (9:1:0.1 v/v) to give the desired compound as a white foam (88%).
MS (TIC): 372.1 (M+H$^+$)

Intermediate

2-[2-(tert-Butyl-dimethyl-silanyloxy)-ethyl]-8-(1-isopropyl-piperidin-4-yloxy)-3,4-dihydro-2H-pyrazino[1,2-a]indol-1-one The title compound was synthesized in analogy to example 17, from 8-(1-isopropyl-piperidin-4-yloxy)-3,4-dihydro-2H-pyrazino[1,2-a]indol-1-one (example 1), sodium hydride and (2-bromoethoxy)-tert-butyldimethylsilane, to give the desired product as a white solid (52%).
MS (TIC): 486.3 (M+H$^+$)

Example 60

(R)-2-Benzyl-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and benzyl bromide, to give the desired product as a light yellow solid (58%).
MS (TIC): 432.2 (M+H$^+$)

Example 61

(R)-8-(1-Isopropyl-piperidin-4-yloxy)-4-methyl-2-pyridin-2-ylmethyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride (2.4 equivalents) and 2-(chloromethyl)pyridine hydrochloride, to give the desired product as a light yellow foam (67%).
MS (TIC): 433.2 (M+H$^+$)

Example 62

(R)-8-(1-Isopropyl-piperidin-4-yloxy)-4-methyl-2-pyridin-3-ylmethyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride (2.4 equivalents) and 3-(chloromethyl)pyridine hydrochloride, to give the desired product as a light yellow foam (61%).
MS (TIC): 433.2 (M+H$^+$)

Example 63

(R)-8-(1-Isopropyl-piperidin-4-yloxy)-4-methyl-2-pyridin-4-ylmethyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride (2.4 equivalents) and 4-(chloromethyl)pyridine hydrochloride, to give the desired product as a light yellow foam (68%).
MS (TIC): 433.2 (M+H$^+$)

Example 64

(R)-8-(1-Isopropyl-piperidin-4-yloxy)-4-methyl-2-(2-methyl-thiazol-4-ylmethyl)-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride (2.4 equivalents) and 4-(chloromethyl)-2-methyl-1,3-thiazole, to give the desired product as a light yellow foam (61%).
MS (TIC): 453.2 (M+H$^+$)

Example 65

(R)-8-(1-Isopropyl-piperidin-4-yloxy)-4-methyl-2-(5-methyl-2-phenyl-oxazol-4-ylmethyl)-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and 4-chloromethyl-5-methyl-2-phenyloxazole, to give the desired product as a brown solid (71%).

MS (TIC): 513.5 (M+H$^+$)

Example 66

(R)-8-(1-Isopropyl-piperidin-4-yloxy)-4-methyl-2-(5-phenyl-[1,2,4]oxadiazol-3-ylmethyl)-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and 3-(chloromethyl)-5-phenyl-1,2,4-oxadiazole, to give the desired product as a brown oil (67%).

MS (TIC): 500.3 (M+H$^+$)

Example 67

(R)-2-(3,5-Dimethyl-isoxazol-4-ylmethyl)-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and 4-(chloromethyl)-3,5-dimethylisoxazol, to give the desired product as a white solid (66%).

MS (TIC): 451.2 (M+H$^+$)

Example 68

(R)-8-(1-Isopropyl-piperidin-4-yloxy)-4-methyl-2-(5-methyl-3-phenyl-isoxazol-4-ylmethyl)-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and 4-(bromomethyl)-5-methyl-3-phenyl-isoxazol, to give the desired product as a brown oil (71%).

MS (TIC): 513.5 (M+H$^+$)

Example 69

(R)-8-(1-Isopropyl-piperidin-4-yloxy)-4-methyl-2-(5-methyl-isoxazol-3-ylmethyl)-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and 3-(bromomethyl)-5-methylisoxazole, to give the desired product as a yellow oil (76%).

MS (TIC): 437.4 (M+H$^+$)

Example 70

(R)-2-(3-Hydroxy-propyl)-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and 3-bromo-1-propanol, to give the desired product as a colorless oil (58%).

MS (TIC): 400.3 (M+H$^+$)

Example 71

(R)-2-(2-Hydroxy-ethyl)-8-(1-isopropyl-piperidin-4-yloxy)-4-methyl-3,4-dihydro-2H-pyrazino[1,2-a]indol-1-one To the solution of 0.14 g (0.28 mmol) (R)-2-[2-(tert-butyl-dimethyl-silanyloxy)-ethyl]-8-(1-isopropyl-piperidin-4-yloxy)-4-methyl-3,4-dihydro-2H-pyrazino[1,2-a]indol-1-one, 98 µL (0.89 g, 0.34 mmol) tetra-n-butylammonium fluoride solution (1M in tetrahydrofuran) was added. After 1 h, the reaction was diluted with dichloromethane and was poured on 1M aqueous sodium hydroxide solution. The organic phase was separated, washed with brine and dried over magnesium sulfate. After filtration the volatile components were removed at a rotary evaporator to give the desired product as a colorless oil (86%).

MS (TIC): 386.2 (M+H$^+$)

Intermediate (R)-2-[2-(tert-Butyl-dimethyl-silanyloxy)-ethyl]-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and (2-bromoethoxy)-tert-butyldimethylsilane, to give the desired product as a colorless oil (500%).

MS (TIC): 500.2 (M+H$^+$)

Example 72

(R)-8-(1-Isopropyl-piperidin-4-yloxy)-4-methyl-2-((R)-4,4,4-trifluoro-3-hydroxy-butyl)-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and (R)-toluene-4-sulfonic acid 4,4,4-trifluoro-3-hydroxy-butyl ester (prepared from commercially available (R)-4,4,4-trifluoro-butane-1,3-diol in analogy to M. Tordeux et. al, J. Fluorine Chem. 20, 301 (1982) and U.S. Pat. No. 5,405,967) to give the desired product as a light yellow oil (5%).

MS (TIC): 468.2 (M+H$^+$)

Example 73

(R)-2-Acetyl-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and acetic anhydride, to give the desired product as a light yellow solid (43%).

MS (TIC): 384.2 (M+H$^+$)

Example 74

(R)-2-Benzenesulfonyl-8-(1-isopropyl-piperidin-4-yloxy)-4-methyl-3,4-dihydro-2H-pyrazino[1,2-a]indol-1-one The title compound was synthesized in analogy to example 17, from (R)-8-(1-isopropyl-piperidin-4-yloxy)-4-methyl-3,4-dihydro-2H-pyrazino[1,2-a]indol-1-one (example 8), sodium hydride and benzenesulfonyl chloride, to give the desired product as a yellow oil (43%).

MS (TIC): 482.4 (M#H$^+$)

Example 75

(S)-2-Cyclopropylmethyl-4-hydroxymethyl-8-(1-isopropyl-piperidin-4-yloxy)-3,4-dihydro-2H-pyrazino[1,2-a]indol-1-one The title compound was synthesized in analogy to example 12, from (S)-2-cyclopropylmethyl-4-[dimethyl-(1,1,2-trimethyl-propyl)-silanyloxymethyl]-8-(1-isopropyl-piperidin-4-yloxy)-3,4-dihydro-2H-pyrazino[1,2-a]indol-1-one and tetra-n-butylammoniumfluoride, to give the desired product as a colorless oil (74%).

MS (TIC): 412.2 (M#H$^+$)

Intermediates (S)-2-Cyclopropylmethyl-4-[dimethyl-(1,1,2-trimethyl-propyl)-silanyloxymethyl]-8-(1-isopropyl-piperidin-4-yloxy)-3,4-dihydro-2H-pyrazino[1,2-a]indol-1-one The title compound was synthesized in analogy to example 17, from (S)-4-[dimethyl-(1,1,2-trimethyl-propyl)-silanyloxymethyl]-8-(1-isopropyl-piperidin-4-yloxy)-3,4-dihydro-2H-pyrazino[1,2-a]indol-1-one (example 12, intermediate a)), sodium hydride and 1-(bromomethyl)cyclopropane, to give the desired product as a colorless oil (38%).

MS (TIC): 554.4 (M#H$^+$)

Example 76

(S)-2-Cyclopropylmethyl-8-(1-isopropyl-piperidin-4-yloxy)-4-methoxymethyl-3,4-dihydro-2H-pyrazino[1,2-a]indol-1-one The title compound was synthesized in analogy to example 17, from (S)-2-cyclopropylmethyl-4-hydroxymethyl-8-(1-isopropyl-piperidin-4-yloxy)-3,4-dihydro-2H-pyrazino[1,2-a]indol-1-one (example 75), methyl iodide and sodium hydride, to give the desired product as a colorless oil (67%).

MS (TIC): 426.4 (M+H$^+$)

Example 77

(S)-4-Hydroxymethyl-8-(1-isopropyl-piperidin-4-yloxy)-2-methyl-3,4-dihydro-2H-pyrazino[1,2-a]indol-1-one The title compound was synthesized in analogy to example 17, from (S)-4-hydroxymethyl-8-(1-isopropyl-piperidin-4-yloxy)-3,4-dihydro-2H-pyrazino[1,2-a]indol-1-one (example 12), methyl iodide and sodium hydride, to give the desired product as a colorless oil (16%).

MS (TIC): 372.1 (M+H$^+$)

Example 78

2-Cyclopropylmethyl-9-(1-isopropyl-piperidin-4-yloxy)-2,3,4,5-tetrahydro-[1,4]diazepino[1,2-a]indol-1-one The title compound was synthesized in analogy to example 1, from 2-cyclopropylmethyl-9-hydroxy-2,3,4,5-tetrahydro-[1,4]diazepino[1,2-a]indol-1-one, 1-isopropyl-piperidin-4-ol (commercially available), triphenylphosphine and di-tert-butylazodicarboxylate, to give the desired product as a light yellow solid (45%).

MS (TIC): 396.1 (M+H$^+$)

Intermediates

2-Cyclopropylmethyl-9-hydroxy-2,3,4,5-tetrahydro-[1,4]diazepino[1,2-a]indol-1-one The title compound was synthesized in analogy to example 11, intermediate a), through hydrogenation of 9-benzyloxy-2-cyclopropylmethyl-2,3,4,5-tetrahydro-[1,4]diazepino[1,2-a]indol-1-one, to give the desired compound as a light yellow solid (73%).

MS (TIC): 271.1 (M+H$^+$)

9-Benzyloxy-2-cyclopropylmethyl-2,3,4,5-tetrahydro-[1,4]diazepino[1,2-a]indol-1-one The title compound was synthesized in analogy to example 17, from 9-benzyloxy-2,3,4,5-tetrahydro-[1,4]diazepino[1,2-a]indol-1-one (example 15, intermediate b)), 1-(bromomethyl)cyclopropane and sodium hydride, to give the compound as a white solid (76%).

MS (TIC): 361.2 (M+H$^+$)

Example 79

9-(1-Isopropyl-piperidin-4-yloxy)-2-(2-methoxy-ethyl)-2,3,4,5-tetrahydro-[1,4]diazepino[1,2-a]indol-1-one The title compound was synthesized in analogy to example 1, from 9-hydroxy-2-(2-methoxy-ethyl)-2,3,4,5-tetrahydro-[1,4]diazepino[1,2-a]indol-1-one, 1-isopropyl-piperidin-4-ol (commercially available), triphenylphosphine and di-tert-butylazodicarboxylate, to give the desired product as a light yellow oil (2%).

MS (TIC): 400.6 (M+H$^+$)

Intermediates

9-Hydroxy-2-(2-methoxy-ethyl)-2,3,4,5-tetrahydro-[1,4]diazepino[1,2-a]indol-1-one The title compound was synthesized in analogy to example 11, intermediate a), through hydrogenation of 9-benzyloxy-2-(2-methoxy-ethyl)-2,3,4,5-tetrahydro-[1,4]diazepino[1,2-a]indol-1-one, to give the compound as a light yellow foam (>100%). The product was used without further purification for the next step.

MS (TIC): 275.0 (M+H$^+$)

9-Benzyloxy-2-(2-methoxy-ethyl)-2,3,4,5-tetrahydro-[1,4]diazepino[1,2-a]indol-1-one The title compound was synthesized in analogy to example 17, from 9-benzyloxy-2,3,4,5-tetrahydro-[1,4]diazepino[1,2-a]indol-1-one (example 15, intermediate b)), 2-bromoethyl methyl ether and sodium hydride, to give the compound as a white solid (77%).

MS (EI): 364.1 (M)

Example 80

2-Cyclopropylmethyl-9-(3-pyrrolidin-1-yl-propoxy)-2,3,4,5-tetrahydro-[1,4]diazepino[1,2-a]indol-1-one The title compound was synthesized in analogy to example 17, from 9-(3-pyrrolidin-1-yl-propoxy)-2,3,4,5-tetrahydro-[1,4]diazepino[1,2-a]indol-1-one (example 16), 1-(bromomethyl)cyclopropane and sodium hydride, to give the desired product as a white solid (29%).

MS (TIC): 382.1 (M+H$^+$)

Example 81

2-(2-Methoxy-ethyl)-9-(3-pyrrolidin-1-yl-propoxy)-2,3,4,5-tetrahydro-[1,4]diazepino[1,2-a]indol-1-one The title compound was synthesized in analogy to example 17, from 9-(3-pyrrolidin-1-yl-propoxy)-2,3,4,5-tetrahydro-[1,4]diazepino[1,2-a]indol-1-one (example 16), 2-bromoethyl methyl ether and sodium hydride, to give the desired product as a colorless oil (15%).

MS (TIC): 386.2 (M+H$^+$)

Example 82

(R)-10-Chloro-8-(1-isopropyl-piperidin-4-yloxy)-4-methyl-3,4-dihydro-2H-pyrazino[1,2-a]indol-1-one To the solution of 0.20 g (0.58 mmol) (R)-8-(1-isopropyl-piperidin-4-yloxy)-4-methyl-3,4-dihydro-2H-pyrazino[1,2-a]indol-1-one (example 8) in 3 mL N,N-dimethylformamide, 86 µg (0.64 mmol) N-chlorosuccinimide were added and the solution was stirred for 18 hours. The reaction mixture was poured on 1M aqueous sodium hydroxide solution and was extracted three times with ethyl acetate. The combined organic layers were washed with brine, dried over magnesium sulfate, filtered and evaporated. The crude product was purified by flash column chromatography on silica gel with dichloromethane: methanol:ammonia (9:1:0.1 v/v) as eluant to give 81 µg (37%) of the desired compound as a colorless oil.

MS (TIC): 376.2 (M+H$^+$)

Example 83

(R)-10-Bromo-8-(1-isopropyl-piperidin-4-yloxy)-4-methyl-3,4-dihydro-2H-pyrazino[1,2-a]indol-1-one The title compound was synthesized in analogy to example 82, from (R)-8-(1-isopropyl-piperidin-4-yloxy)-4-methyl-3,4-dihydro-2H-pyrazino[1,2-a]indol-1-one (example 8) and N-bromosuccinimide, to give the desired product as a light yellow oil (69%).

MS (TIC): 420.0 (M+H$^+$)

Example 84

7-(1-Isopropyl-piperidin-4-yloxy)-3,4-dihydro-2H-2,4a,5-triaza-fluoren-1-one The title compound was synthesized in analogy to example 1, from 7-hydroxy-3,4-dihydro-2H-2,4a,5-triaza-fluoren-1-one, 1-isopropyl-piperidin-4-ol (commercially available), triphenylphosphine and di-tert-butylazodicarboxylate, to give the desired product as a white solid (42%).

MS (TIC): 329.1 (M+H$^+$)

Intermediates

7-Hydroxy-3,4-dihydro-2H-2,4a,5-triaza-fluoren-1-one

The suspension consistent of 0.20 g (0.68 mmol) 7-benzyloxy-3,4-dihydro-2H-2,4a,5-triaza-fluoren-1-one and 30 µg palladium on activated charcoal (10% Pd; commercially available) in 2 mL formic acid was hydrogenated at room temperature at 1.5 bar for 3 hours. The reaction mixture was filtered over Dicalite Speed Plus® (Aldrich), the filter cake was washed with formic acid and the volatile components were evaporated at a rotary evaporator. The residue was stirred in 3 mL ethyl acetate, filtered and the light brown product (65%) was dried under high vacuum.

MS (EI): 203.1 (M)

7-Benzyloxy-3,4-dihydro-2H-2,4a,5-triaza-fluoren-1-one

The title compound was synthesized in analogy to example 8, intermediate a), from 5-benzyloxy-1-(2-tert-butoxycarbonylamino-ethyl)-1H-pyrrolo[2,3-b]pyridine-2-carboxylic acid methyl ester, to give the desired product as a colorless solid.

MS (TIC): 294.2 (M+H$^+$)

5-Benzyloxy-1-(2-tert-butoxycarbonylamino-ethyl)-1H-pyrrolo[2,3-b]pyridine-2-carboxylic Acid Methyl Ester The title compound was synthesized in analogy to example 1, intermediate b), from 5-benzyloxy-pyrrolo[2,3-b]pyridine-1,2-dicarboxylic acid 1-tert-butyl ester 2-methyl ester (intermediate M), 2,2-dioxo-[1,2,3]oxathiazolidine-3-carboxylic acid tert-butyl ester (prepared according to WO02/072584) and potassium tert-butoxide, to give the product as a colorless foam (89%).

MS (EI): 425.2 (M); 308.1 (M-(C$_4$H$_8$+CO$_2$+NH$_3$))

Example 85

7-[3-((S)-2-Methyl-pyrrolidin-1-yl)-propoxy]-3,4-dihydro-2H-2,4a,5-triaza-fluoren-1-one The title compound was synthesized in analogy to example 2, from 7-(3-chloro-propoxy)-3,4-dihydro-2H-2,4a,5-triaza-fluoren-1-one and (S)-2-methylpyrrolidine (commercially available), to give the desired product as a colorless solid (19%).
MS (TIC): 329.1 (M+H$^+$)

Intermediate 7-(3-Chloro-propoxy)-3,4-dihydro-2H-2,4a,5-triaza-fluoren-1-one The title compound was synthesized in analogy to example 2, intermediate, from 7-hydroxy-3,4-dihydro-2H-2,4a,5-triaza-fluoren-1-one (example 84, intermediate a) and 1-bromo-3-chloropropane, to give the desired product as a light yellow solid (80%).
MS (TIC): 280.0 (M+H$^+$)

Example 86

7-[3-((R)-2-Methyl-pyrrolidin-1-yl)-propoxy]-3,4-dihydro-2H-2,4a,5-triaza-fluoren-1-one The title compound was synthesized in analogy to example 2, from 7-(3-chloro-propoxy)-3,4-dihydro-2H-2,4a,5-triaza-fluoren-1-one (example 85, intermediate) and (R)-2-methylpyrrolidine (commercially available), to give the desired product as a colorless solid (32%).
MS (TIC): 329.1 (M+H$^+$)

Example 87

7-[3-((2R,5R)-2,5-Dimethyl-pyrrolidin-1-yl)-propoxy]-3,4-dihydro-2H-2,4a,5-triaza-fluoren-1-one The title compound was synthesized in analogy to example 2, from 7-(3-chloro-propoxy)-3,4-dihydro-2H-2,4a,5-triaza-fluoren-1-one (example 85, intermediate) and (2R,5R)-(−)-trans-2,5-dimethylpyrrolidine (commercially available), to give the desired product as a colorless solid (19%).
MS (TIC): 343.0 (M+H$^+$)

Example 88

7-(1-Cyclopropylmethyl-piperidin-4-yloxy)-3,4-dihydro-2H-2,4a,5-triaza-fluoren-1-one To a solution of 0.40 g (1.40 mmol) 7-(piperidin-4-yloxy)-3,4-dihydro-2H-2,4a,5-triaza-fluoren-1-one in 8 mL tetrahydrofuran, 30 μL (30 μg, 1.67 mmol) water, 0.16 mL (0.15 g, 2.11 mmol) cyclopropanecarboxaldehyde, 0.24 mL (0.25 g, 4.2 mmol) acetic acid and 2.1 mL (1.93 g, 2.1 mmol) sodium cyanoborohydride (1M solution in tetrahydrofuran) were added successively and the reaction mixture was stirred for 18 hours at 55° C. After cooling to room temperature the reaction was poured on 10% aqueous sodium bicarbonate solution and was extracted three times with ethyl acetate. The combined organic layers were washed with brine, dried over magnesium sulfate, filtered and evaporated. The residue was flash-chromatographed on silica gel with dichloromethane: methanol: ammonia (9:1:0.1 v/v) as eluant to give 0.19 g (40%) of the desired compound as a white solid.
MS (TIC): 341.1 (M+H$^+$)

Intermediates 7-(Piperidin-4-yloxy)-3,4-dihydro-2H-2,4a,5-triaza-fluoren-1-one The solution of 0.45 g (1.17 mmol) 4-(1-oxo-1,2,3,4-tetrahydro-2,4a,5-triaza-fluoren-7-yloxy)-piperidine-1-carboxylic acid tert-butyl ester in 10 mL dichloromethane was cooled to 0° C., 5 mL (7.4 g, 65.3 mmol) trifluoroacetic acid were added and the cooling bath was removed. After 1 h the volatile components were removed at a rotary evaporator, the residue was dissolved in dichloromethane and was washed with 1M aqueous sodium hydroxide solution and brine. The organic layer was dried over magnesium sulfate, filtered and evaporated to give 140 mg (42%) of the desired product as a white solid.
MS (TIC): 286.0 (M+H$^+$)

4-(1-Oxo-1,2,3,4-tetrahydro-2,4a,5-triaza-fluoren-7-yloxy)-piperidine-1-carboxylic Acid Tert-Butyl Ester The title compound was synthesized in analogy to example 1, from 7-hydroxy-3,4-dihydro-2H-2,4a,5-triaza-fluoren-1-one (example 84, intermediate a)), tert-butyl 4-hydroxy-1-piperidinecarboxylate (commercially available), triphenylphosphine and di-tert-butylazodicarboxylate, to give the desired product as a light brown solid (70%).
MS (TIC): 387.2 (M+H$^+$)

Example 89

2-Cyclopropylmethyl-7-(1-isopropyl-piperidin-4-yloxy)-3,4-dihydro-2H-2,4a,5-triaza-fluoren-1-one The title compound was synthesized in analogy to example 17, from 7-(1-isopropyl-piperidin-4-yloxy)-3,4-dihydro-2H-2,4a,5-triaza-fluoren-1-one (example 84), 1-(bromomethyl)cyclopropane and sodium hydride, to give the desired product as a colorless solid (85%).
MS (TIC): 383.1 (M#H$^+$)

Example 90

7-(1-Isopropyl-piperidin-4-yloxy)-2-(2-methoxy-ethyl)-3,4-dihydro-2H-2,4a,5-triaza-fluoren-1-one The title compound was synthesized in analogy to example 17, from 7-(1-isopropyl-piperidin-4-yloxy)-3,4-dihydro-2H-2,4a,5-triaza-fluoren-1-one (example 84), 2-bromoethyl methyl ether and sodium hydride, to give the desired product as a colorless oil (72%).
MS (TIC): 387.2 (M#H$^+$)

Example 91

7-(1-Isopropyl-piperidin-4-yloxy)-2-(2,2,2-trifluoro-ethyl)-3,4-dihydro-2H-2,4a,5-triaza-fluoren-1-one The title compound was synthesized in analogy to example 17, from 7-(1-isopropyl-piperidin-4-yloxy)-3,4-dihydro-2H-2,4a,5-triaza-fluoren-1-one (example 84), 2,2,2-trifluoroethyl trifluoromethanesulfonate and sodium hydride, to give the desired product as a colorless solid (42%).

MS (TIC): 411.2 (M#H$^+$)

Example 92

7-[3-((S)-2-Methyl-pyrrolidin-1-yl)-propoxy]-2-(2,2,2-trifluoro-ethyl)-3,4-dihydro-2H-2,4a,5-triaza-fluoren-1-one The title compound was synthesized in analogy to example 17, from 7-[3-((S)-2-methyl-pyrrolidin-1-yl)-propoxy]-3,4-dihydro-2H-2,4a,5-triaza-fluoren-1-one (example 85), 2,2,2-trifluoroethyl trifluoromethanesulfonate and sodium hydride, to give the desired product as a colorless solid (12%).

MS (TIC): 411.2 (M+H$^+$)

Intermediates

Intermediate E

5-Benzyloxy-6-chloro-pyrrolo[2,3-b]pyridine-1,2-dicarboxylic acid 1-tert-butyl ester 2-methyl Ester The solution of 17.2 g (91.0 mmol) 6-amino-5-bromo-pyridin-3-ol (prepared according to WO98/25920) in 175 ml N,N-dimethylformamide was cooled to 0° C. and treated in portions with 4.17 g (96.0 mmol; 55% dispersion in mineral oil) sodium hydride. Another 75 ml N,N-dimethylformamide were added and after 30 min. stirring at room temperature, the mixture was cooled to 0° C. and 11.4 ml (96.0 mmol) benzyl bromide were added dropwise. The cooling bath was removed and after 60 min. at room temperature the reaction mixture was poured on 10% aqueous ammonium chloride solution and was extracted three times with ethyl acetate. The combined organic layers were washed with water and brine, dried over magnesium sulfate and evaporated. The crude product was purified by flash column chromatography with n-heptane:ethyl acetate (1:1 v/v) as eluant. The suspension formed during evaporation was filtered and the filter cake was washed with n-heptane to give 16.2 g (63%) of the product as a colorless solid. The remaining pale yellow mother liquor contained another 4.2 g (16%) of the product which were pure enough for the next step.

MS (EI): 278.0; 280.0 (M)

Intermediate F

5-Benzyloxy-3-{3-[dimethyl-(1,1,2-trimethyl-propyl)-silanyloxy]-prop-1-ynyl}-pyridin-2-ylamine The mixture of 0.29 g (1.54 mmol) copper iodide and bis(triphenylphosphine) palladium(II) chloride in 215 ml triethylamine was stirred 15 min. under reflux. The mixture was cooled to 40° C., then 21.5 g (77.0 mmol) 5-benzyloxy-6-chloro-pyrrolo[2,3-b]pyridine-1,2-dicarboxylic acid 1-tert-butyl ester 2-methyl ester and 18.6 g (94.0 mmol) dimethyl-prop-2-ynyloxy-(1,1,2-trimethyl-propyl)-silane were added and the reaction mixture was refluxed for 19 h. After cooling down to room temperature the suspension was poured on 10% aqueous citric acid solution and extracted three times with ethyl acetate. The combined organic layers were washed with brine, dried over magnesium sulfate and evaporated. The residue was flash-chromatographed on silica gel with acetone: n-heptane (1:2 v/v) as eluant to give 13.7 g (45%) of the product as brown solid together with some starting material (ca 8.7 g) which could be used again for the same reaction.

MS (EI): 396.3 (M); 311.1 (M-C$_6$H$_{13}$)

Intermediate G

5-Benzyloxy-2-[dimethyl-(1,1,2-trimethyl-propyl)-silanyloxymethyl]-1H-pyrrolo[2,3-b]pyridine The solution of 1.0 g (2.5 mmol) 5-benzyloxy-3-{3-[dimethyl-(1,1,2-trimethyl-propyl)-silanyloxy]-prop-1-ynyl}-pyridin-2-ylamine in 25 ml dichloromethane at 0° C. was treated with 0.39 ml (0.58 g, 1.10 mmol) trifluoroacetic anhydride. The cooling bath was removed and after stirring for 60 min. at room temperature the volatile components were removed at a rotary evaporator. The remaining light brown oil was dissolved in 25 ml triethylamine and 14 mg (73.5 μmol) copper (I) iodide and 18 mg (25.6 μmol) bis(triphenylphosphine) palladium(II) chloride were added and the mixture was stirred at reflux temperature for 20 h. The mixture was poured on 10% aqueous ammonium chloride solution and extracted three times with ethyl acetate. The combined organic layers were washed with water and brine, dried over magnesium sulfate, filtered and evaporated. The crude product was purified by flash chromatography with acetone:n-heptane (1:3 v/v) as eluant to give 0.5 g (45%) of the desired compound as a yellow solid.

MS (EI): 396.2 (M); 311.1 (M-C$_6$H$_{13}$)

Intermediate H

(5-Benzyloxy-1H-pyrrolo[2,3-b]pyridin-2-yl)-methanol

To the solution of 0.53 g (1.3 mmol) 5-benzyloxy-2-[dimethyl-(1,1,2-trimethyl-propyl)-silanyloxymethyl]-1H-pyrrolo[2,3-b]pyridine in 3 ml tetrahydrofuran 1.6 ml (1.6 mmol) tetra-n-butylammonium fluoride (1M solution in tetrahydrofuran) were added. After 75 min. the solution was poured on saturated aqueous sodium bicarbonate solution and was extracted three times with ethyl acetate. The combined organic layers were washed with brine, dried over magnesium sulfate, filtered and evaporated. The residue was stirred in tert-butyl methyl ether, filtered and washed with tert-butyl methyl ether to give 0.3 g (88%) of the product as a brown solid.

MS (EI): 254.1 (M)

Intermediate J

5-Benzyloxy-1H-pyrrolo[2,3-b]pyridine-2-carbaldehyde

The suspension of 0.3 g (1.2 mmol) (5-benzyloxy-1H-pyrrolo[2,3-b]pyridin-2-yl)-methanol and 0.82 g (9.4 mmol) manganese dioxide in 15 ml dichloromethane was stirred 3 h at room temperature. After filtration over Dicalite Speed Plus® (Aldrich) the solvent was evaporated to give 0.22 g (74%) of the desired compound as a light brown solid.

MS (EI): 252.1 (M)

Intermediate K

5-Benzyloxy-2-formyl-pyrrolo[2,3-b]pyridine-1-carboxylic Acid Tert-Butyl Ester To the suspension of 0.42 g (1.7 mmol) 5-benzyloxy-1H-pyrrolo[2,3-b]pyridine-2-carbaldehyde in 10 ml dichloromethane 0.38 g (1.75 mmol) di-tert-butyl dicarbonate and 10 mg (82 μmol) 4-(dimethylamino)pyridine were added. After 20 min. a solution had formed which was evaporated.

The residue was flash-chromatographed on silica gel with n-heptane: ethyl:acetate (2:1 v/v). Upon evaporation a suspension formed which was cooled to 5° C. and filtered. The filter cake was washed with n-heptane and dried under vacuum to give 0.4 g (69%) of the product as a light brown solid.

MS (EI): 352.1 (M); 252.1 (M-($C_4H_8$+$CO_2$))

Intermediate L

5-Benzyloxy-pyrrolo[2,3-b]pyridine-1,2-dicarboxylic acid 1-tert-butyl Ester

To the solution of 0.41 g (1.2 mmol) 5-benzyloxy-2-formyl-pyrrolo[2,3-b]pyridine-1-carboxylic acid tert-butyl ester in 10 ml tert-butanol, 7 ml 2-methyl-2-butene and 20 ml acetonitrile, a mixture consistent of 1.2 g (10.6 mmol; 80%) sodium chlorite and 0.97 g (8.1 mmol) sodium dihydrogen phosphate in 10 ml water was added dropwise. The resulting two-phase mixture was stirred 1.5 h at room temperature. Then the organic components were evaporated at a rotary evaporator and the remaining aqueous phase was extracted three times with dichloromethane. The combined organic layers were washed with 10% aqueous sodium thiosulfate solution and brine, dried over magnesium sulfate, filtered and evaporated. The crude product was purified by flash-chromatography on silica gel with ethyl acetate: n-heptane (1:1 v/v) as eluant to give 0.35 g (74%) of the compound as a yellow foam.

MS (TIC): 367.1 (M−H)

Intermediate M

5-Benzyloxy-pyrrolo[2,3-b]pyridine-1,2-dicarboxylic acid 1-tert-butyl ester 2-methyl Ester The solution of 0.2 g (0.54 mmol) 5-benzyloxy-pyrrolo[2, 3-b]pyridine-1,2-dicarboxylic acid 1-tert-butyl ester in 2 ml N,N-dimethylformamide was cooled down to 0° C. and 26 mg (0.54 mmol; 55% dispersion in mineral oil) sodium hydride were added. After 15 min., 38 μl (85 mg, 0.6 mmol) methyl iodide were added and the cooling bath was removed. After 5 hours the reaction mixture was poured on water and was extracted five times with dichloromethane. The organic layers were dried over magnesium sulfate, filtered and evaporated to give 0.19 g (93%) the compound as a light yellow oil which was pure enough for the subsequent steps without further purification.

MS (TIC): 383.0 (M+H$^+$)

Intermediate N

5-Benzyloxy-1H-pyrrolo[2,3-b]pyridine-2-carboxylic Acid Methyl Ester

The suspension of 0.2 g (0.54 mmol) 5-benzyloxy-pyrrolo [2,3-b]pyridine-1,2-dicarboxylic acid 1-tert-butyl ester (intermediate G) and 30 μl of concentrated sulfuric acid in 2 ml methanol was heated under reflux. After 1.5 h another 2 ml methanol and 30 μl of concentrated sulfuric acid were added. The resulting clear solution was refluxed 3 hours and after cooling down to room temperature was poured on saturated sodium bicarbonate solution and extracted three times with ethyl acetate. The combined organic layers were washed with brine, dried over magnesium sulfate, filtered and evaporated to give 0.12 g (78%) of the product as a colorless solid.

MS (TIC): 282.8 (M+H$^+$)

Example 93

(R)-7-Bromo-8-(1-isopropyl-piperidin-4-yloxy)-4-methyl-3,4-dihydro-2H-pyrazino[1,2-a]indol-1-one The solution of 0.21 g (0.37 mmol) 6-bromo-1-(2-tert-butoxycarbonylamino-1-methyl-ethyl)-5-(1-isopropyl-piperidin-4-yloxy)-1H-indole-2-carboxylic acid ethyl ester in 4 mL dichloromethane was cooled to 0° C. and 2 mL (2.98 g, 26.1 mmol) trifluoroacetic acid were added dropwise within 5 min. The cooling bath was removed and after 1 h the volatile components were removed at a rotary evaporator. The residue was dissolved in 4 mL methanol and 0.2 g (1.48 mmol) potassium carbonate was added under cooling. The suspension was stirred for 72 hours at room temperature and then diluted with water. The solution was extracted three times with ethyl acetate and the combined organic layers were washed with brine, dried over magnesium sulfate, filtered and evaporated. The residue was flash-chromatographed on silica gel with a gradient of dichloromethane:methanol (100:0 to 50:50 v/v) to give 49 mg (31%) of the product as a white solid.

MS (ISP): 420.0 (M+H$^+$)

Intermediates (R)-6-Bromo-1-(2-tert-butoxycarbonylamino-1-methyl-ethyl)-5-(1-isopropyl-piperidin-4-yloxy)-1H-indole-2-carboxylic Acid Ethyl Ester The title compound was synthesized in analogy to example 1, intermediate b), from 6-bromo-5-(1-isopropyl-piperidin-4-yloxy)-1H-indole-2-carboxylic acid ethyl ester, (S)-5-methyl-2,2-dioxo[1,2,3]oxathiazolidine-3-carboxylic acid tert-butyl ester (prepared according to WO 02/010169) and potassium tert-butoxide, to give the desired compound as a light yellow oil (53%). The thus obtained crude product was used without further purification for the next step.

6-Bromo-5-(1-isopropyl-piperidin-4-yloxy)-1H-indole-2-carboxylic Acid Ethyl Ester To the suspension of 0.25 g (0.88 mmol) 6-bromo-5-hydroxy-1H-indole-2-carboxylic acid ethyl ester in 5 mL tetrahydrofuran, 0.15 g (1.05 mmol) 1-isopropyl-piperidin-4-ol (commercially available) and 0.28 g (1.07 mmol) tributylphosphine were added. The suspension was cooled to 0° C., 0.244 g (1.06 mmol) di-tert-butyl azodicarboxylate was added and the reaction was allowed to reach room temperature. After 48 hours the suspension was filtered and the filtrate was evaporated. The residue was flash-chromatographed on silica gel with a gradient of dichloromethane:methanol (100:0 to 60:40 v/v) to give 0.20 g (55%) of the product as a light yellow foam.

MS (ISP): 409.0 (M+H$^+$)

6-Bromo-5-hydroxy-1H-indole-2-carboxylic Acid Ethyl Ester

The solution of 8.30 g (27.8 mmol) 6-bromo-5-methoxy-1H-indole-2-carboxylic acid ethyl ester (prepared according to J. Org. Chem. 1974, 39, 3580) in 160 mL dichloromethane was cooled to −78° C. At this temperature, 55.7 mL boron tribromide (55.7 mmol; 1M solution in dichloromethane) were added. The solution was allowed to warm to room temperature and after 30 min. the solution was poured on 10% aqueous sodium bicarbonate solution, the phases were separated and the aqueous phase was extracted three times with ethyl acetate. The combined organic layers were washed with water followed by brine, dried over magnesium sulfate, filtered and evaporated. The residue was flash-chromatographed on silica gel with n-hexane:ethyl:acetate (2:1 v/v) as eluant to give 5.7 g (72%) of the product as a light yellow solid.

MS (ISP): 282.2 (M–H$^+$)

Example 94

(R)-7-Bromo-2-cyclopropylmethyl-8-(1-isopropyl-piperidin-4-yloxy)-4-methyl-3,4-dihydro-2H-pyrazino[1,2-a]indol-1-one The title compound was synthesized in analogy to example 17, from (R)-7-bromo-8-(1-isopropyl-piperidin-4-yloxy)-4-methyl-3,4-dihydro-2H-pyrazino[1,2-a]indol-1-one (example 93), sodium hydride and 1-(bromomethyl)cyclopropane, to give the product as a white solid (55%).

MS (ISP): 474.0 (M+H$^+$)

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of formula I:

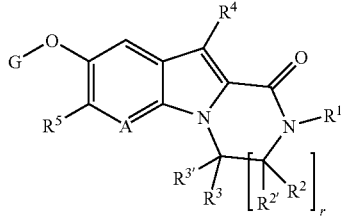

wherein:

A is CH or N;

r is 2;

$R^1$ is selected from the group consisting of hydrogen,
lower alkyl,
lower hydroxyalkyl, lower alkoxyalkyl,
lower halogenalkyl, lower hydroxyhalogenalkyl,
lower alkanoyl,
lower alkylsulfonyl, lower phenylsulfonyl,
lower cycloalkylalkyl,
lower phenylalkyl, wherein the phenyl ring may be unsubstituted or substituted with one or two groups independently selected from lower alkyl, cyano, halogen, lower halogenalkyl, lower alkoxy and lower hydroxyalkyl,
lower heteroarylalkyl, wherein the heteroaryl ring may be unsubstituted or substituted with one or two groups independently selected from lower alkyl, halogen, phenyl, lower alkoxy and lower hydroxyalkyl,
lower heterocyclylalkyl, wherein the heterocyclyl ring may be unsubstituted or substituted with one or two groups independently selected from lower alkyl, halogen, phenyl, lower alkoxy and lower hydroxyalkyl, and
—$CH_2$—CO—$NR^{14}R^{15}$, wherein
$R^{14}$ and $R^{15}$ independently from each other are selected from the group hydrogen, lower alkyl and phenyl unsubstituted or substituted with one or two groups independently selected from lower alkyl, halogen, lower halogenoalkoxy and lower hydroxyalkyl,
or $R^{14}$ and $R^{15}$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group,
said heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl;

$R^2$, $R^{2'}$, $R^3$ and $R^{3'}$ independently from each other are selected from the group consisting of hydrogen, lower alkyl, lower hydroxyalkyl and lower alkoxyalkyl;

$R^4$ is selected from the group consisting of hydrogen and halogen;

$R^5$ is hydrogen or halogen;

G is a group selected from

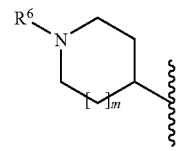

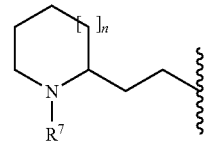

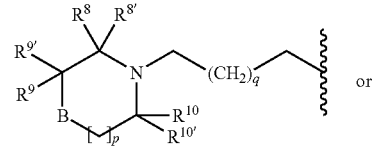

or

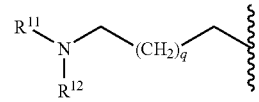

wherein m is 0, 1 or 2;

$R^6$ is selected from lower alkyl, cycloalkyl, lower cycloalkylalkyl and lower phenylalkyl;

n is 0, 1 or 2;

$R^7$ is lower alkyl;

B is selected from $CR^{13}R^{13'}$, O and S;

$R^8$, $R^{8'}$, $R^9$, $R^{9'}$, $R^{10}$, $R^{10'}$, $R^{13}$ and $R^{13'}$ independently from each other are selected from the group consisting of hydrogen, lower alkyl, hydroxy, halogen and dialkylamino, or
$R^9$ and $R^{13}$ together form a double bond;

p is 0, 1 or 2;

q is 0, 1 or 2;

$R^{11}$ is lower alkyl;

$R^{12}$ is lower alkyl;

or a pharmaceutically acceptable salt thereof.

2. The compound according to claim 1, wherein $R^1$ is selected from the group consisting of hydrogen,
lower alkyl,
lower hydroxyalkyl, lower alkoxyalkyl,
lower halogenalkyl, lower hydroxyhalogenalkyl,
lower alkanoyl,
lower alkylsulfonyl, lower phenylsulfonyl,
lower cycloalkylalkyl,
lower phenylalkyl, wherein the phenyl ring may be unsubstituted or substituted with one or two groups independently selected from lower alkyl, cyano, halogen, lower halogenalkyl, lower alkoxy and lower hydroxyalkyl, and
lower heteroarylalkyl, wherein the heteroaryl ring may be unsubstituted or substituted with one or two groups independently selected from lower alkyl, halogen, phenyl, lower alkoxy and lower hydroxyalkyl.

3. The compound according to claim 1, wherein $R^1$ is selected from the group consisting of hydrogen, lower alkyl, lower hydroxyalkyl, lower alkoxyalkyl, lower halogenalkyl, lower hydroxyhalogenalkyl, lower alkanoyl, lower alkylsulfonyl, lower phenylsulfonyl and lower cycloalkylalkyl.

4. The compound according to claim 1, wherein $R^1$ is lower phenylalkyl, wherein the phenyl ring may be unsubstituted or substituted with one or two groups independently selected from lower alkyl, cyano, halogen, lower halogenalkyl, lower alkoxy and lower hydroxyalkyl.

5. The compound according to claim 1, wherein $R^1$ is lower heteroarylalkyl, wherein the heteroaryl ring may be unsubstituted or substituted with one or two groups independently selected from lower alkyl, halogen, phenyl, lower alkoxy and lower hydroxyalkyl.

6. The compound according to claim 1, wherein $R^1$ is $-CH_2-CO-NR^{14}R^{15}$, wherein $R^{14}$ and $R^{15}$ independently from each other are selected from the group hydrogen, lower alkyl and phenyl unsubstituted or substituted with one or two groups independently selected from lower alkyl, lower halogenalkoxy and lower hydroxyalkyl, or $R^{14}$ and $R^{15}$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted by one, two or three groups independently selected from lower alkyl, halogen, halogenalkyl, hydroxy, lower hydroxyalkyl, lower alkoxy, oxo, phenyl, benzyl, pyridyl and carbamoyl.

7. The compound according to claim 1, wherein one of $R^2$, $R^{2'}$, $R^3$ and $R^{3'}$ is selected from the group consisting of lower alkyl, lower hydroxyalkyl and lower alkoxyalkyl.

8. The compound according to claim 1, wherein $R^4$ is hydrogen.

9. The compound according to claim 1, wherein $R^5$ is hydrogen.

10. The compound according to claim 1, wherein A signifies C.

11. The compound according to claim 1, wherein A signifies N.

12. The compound according to claim 1, wherein G signifies

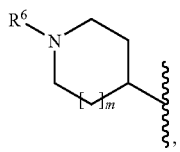

wherein m is 0, 1 or 2, and $R^6$ is selected from the group consisting of lower alkyl, cycloalkyl, lower cycloalkylalkyl and lower phenylalkyl.

13. The compound according to claim 1, wherein $R^6$ is lower alkyl.

14. The compound according to claim 1, wherein G signifies

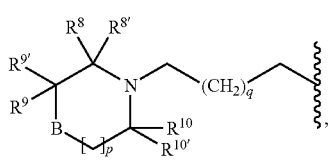

wherein p is 0, 1 or 2; q is 0, 1 or 2; B is selected from $CR^{13}R^{13'}$, O and S; and $R^8$, $R^{8'}$, $R^9$, $R^{9'}$, $R^{10}$, $R^{10'}$, $R^{13}$ and $R^{13'}$ independently from each other are selected from the group consisting of hydrogen, lower alkyl, hydroxy, halogen and dialkylamino, or $R^9$ and $R^{13}$ together form a double bond.

15. The compound according to claim 1, wherein p is 0 or 1, q is 0, B is $CR^{13}R^{13'}$ and $R^8$, $R^{8'}$, $R^9$, $R^{9'}$, $R^{10}$, $R^{10'}$, $R^{13}$ and $R^{13'}$ independently from each other are selected from the group consisting of hydrogen, lower alkyl, hydroxy, halogen and dialkylamino.

16. The compound according to claim 1, wherein G signifies

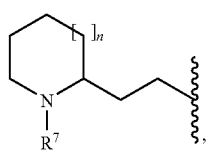

wherein n is 0, 1 or 2; and $R^7$ is lower alkyl.

17. The compound according to claim 1, wherein G signifies

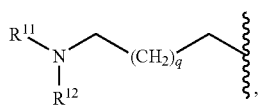

wherein q is 0, 1 or 2, $R^{11}$ is lower alkyl and $R^{12}$ is lower alkyl.

18. The compound according to claim 1, selected from the group consisting of
9-(1-isopropyl-piperidin-4-yloxy)-2,3,4,5-tetrahydro-[1,4]diazepino[1,2-a]indol-1-one,
9-(3-pyrrolidin-1-yl-propoxy)-2,3,4,5-tetrahydro-[1,4]diazepino[1,2-a]indol-1-one,
2-cyclopropylmethyl-9-(1-isopropyl-piperidin-4-yloxy)-2,3,4,5-tetrahydro-[1,4]diazepino[1,2-a]indol-1-one,
9-(1-isopropyl-piperidin-4-yloxy)-2-(2-methoxy-ethyl)-2,3,4,5-tetrahydro-[1,4]diazepino[1,2-a]indol-1-one,
2-cyclopropylmethyl-9-(3-pyrrolidin-1-yl-propoxy)-2,3,4,5-tetrahydro-[1,4]diazepino[1,2-a]indol-1-one, and
2-(2-methoxy-ethyl)-9-(3-pyrrolidin-1-yl-propoxy)-2,3,4,5-tetrahydro-[1,4]diazepino[1,2-a]indol-1-one,
or a pharmaceutically acceptable salt thereof.

19. The compound according to claim 1, wherein said compound is
9-(1-isopropyl-piperidin-4-yloxy)-2,3,4,5-tetrahydro-[1,4]diazepino[1,2-a]indol-1-one,
or a pharmaceutically acceptable salt thereof.

20. A pharmaceutical composition, comprising a therapeutically effective amount of a compound according to claim 1 as well as a pharmaceutically acceptable carrier and/or adjuvant.

* * * * *